(12) United States Patent
Scott et al.

(10) Patent No.: US 9,144,452 B2
(45) Date of Patent: Sep. 29, 2015

(54) ROBOTIC SURGICAL TOOL FOR PLUGGABLE END-EFFECTORS

(75) Inventors: Manzo Scott, Shelton, CT (US); Lisa Heaton, Huntington, CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 127 days.

(21) Appl. No.: 12/753,221

(22) Filed: Apr. 2, 2010

(65) Prior Publication Data

US 2010/0191250 A1    Jul. 29, 2010

Related U.S. Application Data

(60) Division of application No. 11/238,698, filed on Sep. 28, 2005, now Pat. No. 8,398,634, which is a continuation-in-part of application No. 10/126,451, filed on Apr. 18, 2002, now Pat. No. 6,994,708, and a continuation-in-part of application No. 10/611,411, filed on Jun. 30, 2003, now Pat. No. 7,367,973.

(60) Provisional application No. 60/617,341, filed on Oct. 8, 2004.

(51) Int. Cl.
*A61B 19/00* (2006.01)
*A61B 18/14* (2006.01)
*A61B 17/00* (2006.01)
(Continued)

(52) U.S. Cl.
CPC ............. *A61B 18/14* (2013.01); *A61B 18/1445* (2013.01); *A61B 19/2203* (2013.01); *A61B 19/5212* (2013.01); *A61B 2017/00477* (2013.01); *A61B 2017/2945* (2013.01); *A61B 2018/00083* (2013.01); *A61B 2018/146* (2013.01); *A61B 2018/1432* (2013.01); *A61B 2019/2223* (2013.01); *A61B 2019/2234* (2013.01);
(Continued)

(58) Field of Classification Search
CPC ............... A61B 2019/2203; A61B 2019/2223; A61B 2019/2234; A61B 2019/2242; A61B 2019/2246; A61B 2018/146; A61B 18/1445; A61B 18/14; A61B 2018/00083; A61B 2018/1432; A61B 2017/00477; A61B 2017/2945
USPC ....................... 606/1, 41, 45, 50–52, 205–207
See application file for complete search history.

(56) References Cited

U.S. PATENT DOCUMENTS 3,762,019 A    10/1973  Epstein
4,281,447 A     8/1981  Miller et al.
(Continued)

FOREIGN PATENT DOCUMENTS

WO    WO-9950721    10/1999

OTHER PUBLICATIONS

U.S. Appl. No. 09/399,457, filed Sep. 17, 1999 (now abandoned), Ramans, Andris D.
(Continued)

*Primary Examiner* — Michael Peffley
*Assistant Examiner* — Samantha Good

(57) ABSTRACT

In one embodiment of the invention, a replaceable electrosurgical end effector cartridge is provided to couple to a mechanical wrist of a surgical instrument for a robotic surgical system. The replaceable electrosurgical end effector cartridge includes two pluggable end effectors and a pair of spring latches. The two end effectors are moveable end effectors having a jaw portion, an off-center portion, and a base portion in one embodiment. The replaceable electrosurgical end effector cartridge may further include a fastener to rotatably couple the end effectors together.

12 Claims, 14 Drawing Sheets

(51) Int. Cl.
    *A61B 17/29*            (2006.01)
    *A61B 18/00*            (2006.01)

(52) U.S. Cl.
    CPC . *A61B2019/2242* (2013.01); *A61B 2019/2246* (2013.01)

(56) References Cited

U.S. PATENT DOCUMENTS

| | | |
|---|---|---|
| 4,332,066 A | 6/1982 | Hailey et al. |
| 4,360,245 A | 11/1982 | Nikitas |
| 4,486,928 A | 12/1984 | Tucker et al. |
| 4,500,065 A | 2/1985 | Hennekes et al. |
| 4,512,709 A | 4/1985 | Hennekes et al. |
| 4,706,372 A | 11/1987 | Ferrero et al. |
| 4,710,093 A | 12/1987 | Zimmer et al. |
| 4,793,053 A | 12/1988 | Zuccaro et al. |
| 4,809,747 A | 3/1989 | Choly et al. |
| 4,830,569 A | 5/1989 | Jannborg |
| 5,018,266 A | 5/1991 | Hutchinson et al. |
| 5,174,300 A | 12/1992 | Bales et al. |
| 5,184,601 A | 2/1993 | Putman |
| 5,294,209 A | 3/1994 | Naka et al. |
| 5,313,935 A | 5/1994 | Kortenbach et al. |
| 5,372,147 A | 12/1994 | Lathrop, Jr. et al. |
| 5,429,596 A | 7/1995 | Arias et al. |
| 5,445,166 A | 8/1995 | Taylor |
| 5,496,315 A | 3/1996 | Weaver et al. |
| 5,507,297 A | 4/1996 | Slater et al. |
| 5,620,459 A | 4/1997 | Lichtman |
| 5,630,812 A | 5/1997 | Ellman et al. |
| 5,649,956 A | 7/1997 | Jensen et al. |
| 5,662,647 A | 9/1997 | Crow et al. |
| 5,792,135 A | 8/1998 | Madhani et al. |
| 5,797,900 A | 8/1998 | Madhani et al. |
| 5,800,423 A | 9/1998 | Jensen |
| 5,807,378 A | 9/1998 | Jensen et al. |
| 5,808,665 A | 9/1998 | Green |
| 5,855,583 A | 1/1999 | Wang et al. |
| 5,895,386 A | 4/1999 | Odell et al. |
| 5,976,122 A | 11/1999 | Madhani et al. |
| 6,004,509 A | 12/1999 | Dey et al. |
| 6,006,633 A | 12/1999 | Kaiser et al. |
| 6,007,570 A | 12/1999 | Sharkey et al. |
| 6,083,222 A | 7/2000 | Klein et al. |
| 6,090,107 A | 7/2000 | Borgmeier et al. |
| 6,102,909 A | 8/2000 | Chen et al. |
| 6,108,845 A | 8/2000 | Hung et al. |
| 6,113,596 A | 9/2000 | Hooven et al. |
| 6,132,368 A | 10/2000 | Cooper |
| 6,132,441 A | 10/2000 | Grace |
| 6,152,923 A | 11/2000 | Ryan |
| 6,162,220 A | 12/2000 | Nezhat |
| 6,206,903 B1 | 3/2001 | Ramans |
| 6,246,200 B1 | 6/2001 | Blumenkranz et al. |
| 6,309,397 B1 | 10/2001 | Julian et al. |
| 6,312,435 B1 | 11/2001 | Wallace et al. |
| 6,331,181 B1 | 12/2001 | Tierney et al. |
| 6,364,888 B1 | 4/2002 | Niemeyer et al. |
| 6,394,998 B1 | 5/2002 | Wallace et al. |
| 6,406,476 B1 | 6/2002 | Kirwan, Jr. et al. |
| 6,419,675 B1 | 7/2002 | Gallo, Sr. |
| 6,424,885 B1 | 7/2002 | Niemeyer et al. |
| 6,436,107 B1 | 8/2002 | Wang et al. |
| 6,458,130 B1 | 10/2002 | Frazier et al. |
| 6,464,701 B1 | 10/2002 | Hooven et al. |
| 6,488,680 B1 | 12/2002 | Francischelli et al. |
| 6,491,691 B1 | 12/2002 | Morley et al. |
| 6,491,701 B2 | 12/2002 | Tierney et al. |
| 6,511,480 B1 | 1/2003 | Tetzlaff et al. |
| 6,554,844 B2 | 4/2003 | Lee et al. |
| 6,616,604 B1 | 9/2003 | Bass et al. |
| 6,676,669 B2 | 1/2004 | Charles et al. |
| 6,702,805 B1 | 3/2004 | Stuart |
| 6,714,839 B2 | 3/2004 | Salisbury, Jr. et al. |
| 6,720,988 B1 | 4/2004 | Gere et al. |
| 6,746,443 B1 | 6/2004 | Morley et al. |
| 6,758,843 B2 | 7/2004 | Jensen |
| 6,783,524 B2 | 8/2004 | Anderson et al. |
| 6,788,018 B1 | 9/2004 | Blumenkranz |
| 6,817,974 B2 | 11/2004 | Cooper et al. |
| 6,840,938 B1 | 1/2005 | Morley et al. |
| 6,994,708 B2 | 2/2006 | Manzo |
| 7,121,781 B2 | 10/2006 | Sanchez |
| 7,306,597 B2 | 12/2007 | Manzo |
| 7,367,973 B2 | 5/2008 | Manzo et al. |
| 7,824,401 B2 | 11/2010 | Manzo et al. |
| 8,105,320 B2 | 1/2012 | Scott et al. |
| 8,398,634 B2 | 3/2013 | Scott et al. |
| 8,827,996 B2 | 9/2014 | Scott et al. |
| 2002/0111621 A1 | 8/2002 | Wallace et al. |
| 2002/0128632 A1 | 9/2002 | Cucin |
| 2003/0023285 A1 | 1/2003 | Eggers et al. |
| 2006/0074406 A1 | 4/2006 | Cooper et al. |
| 2006/0079889 A1 | 4/2006 | Scott |
| 2006/0167440 A1 | 7/2006 | Cooper et al. |
| 2010/0191251 A1 | 7/2010 | Scott et al. |
| 2010/0198218 A1 | 8/2010 | Manzo |
| 2013/0158542 A1 | 6/2013 | Manzo et al. |

OTHER PUBLICATIONS

U.S. Appl. No. 60/111,713, filed Dec. 8, 1998, Younge, Robert G.
U.S. Appl. No. 60/617,341, filed Oct. 8, 2004, Manzo, Scott et al.
U.S. Appl. No. 60/111,711, filed Dec. 8, 1998, Neimeyer, Gunter.
U.S. Appl. No. 60/431,636, filed Dec. 6, 2002, Cooper, Thomas G. et al.
U.S. Appl. No. 60/285,485, filed Apr. 19, 2001, Anderson, Stephen C.
U.S. Appl. No. 11/238,698 Final Office Action mailed Dec. 4, 2009, 22 pages.
U.S. Appl. No. 11/238,698 Office Action mailed Apr. 13, 2009, 16 pages.
U.S. Appl. No. 11/238,698 Office Action mailed Oct. 3, 2008, 18 pages.
Vertut, Jean et al., "Robot Technology: Teleoperation and Robotics Evolution and Development—vol. 3A", English translation Prentice-Hall, Inc., Inglewood Cliffs, NJ, USA 1986, vol. 3A, 332 pages.
U.S. Appl. No. 11/238,794 Final Office Action mailed Dec. 4, 2009, 15 pages.
U.S. Appl. No. 11/238,794 Office Action mailed May 4, 2009, 14 pages.

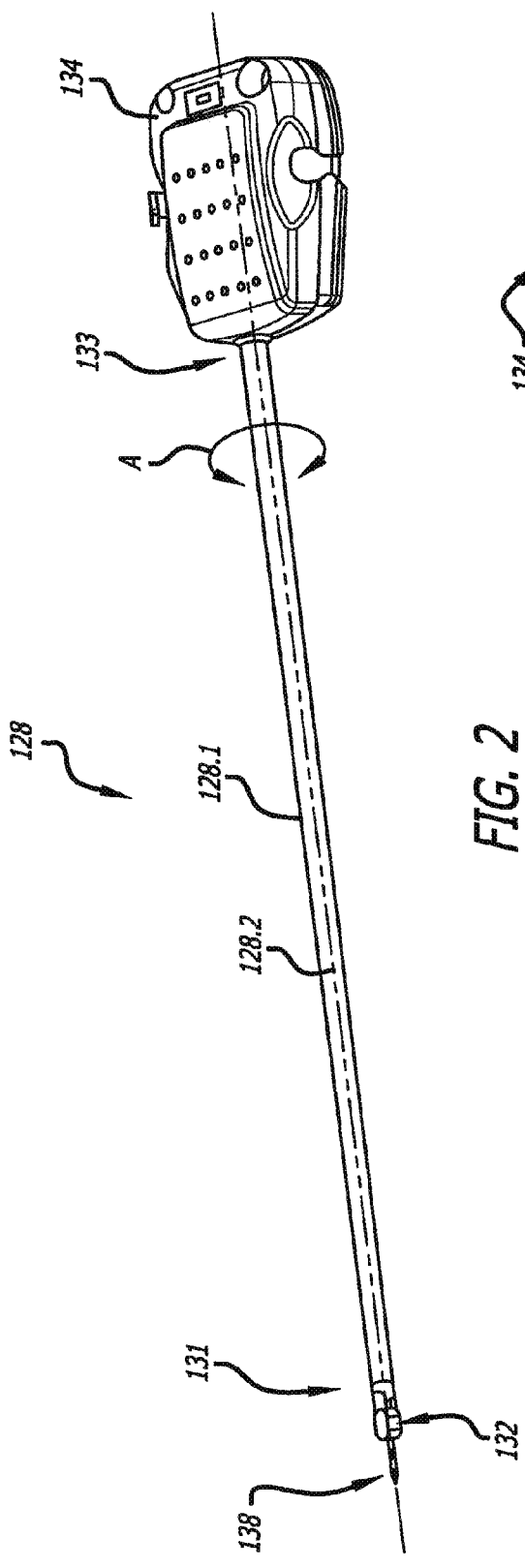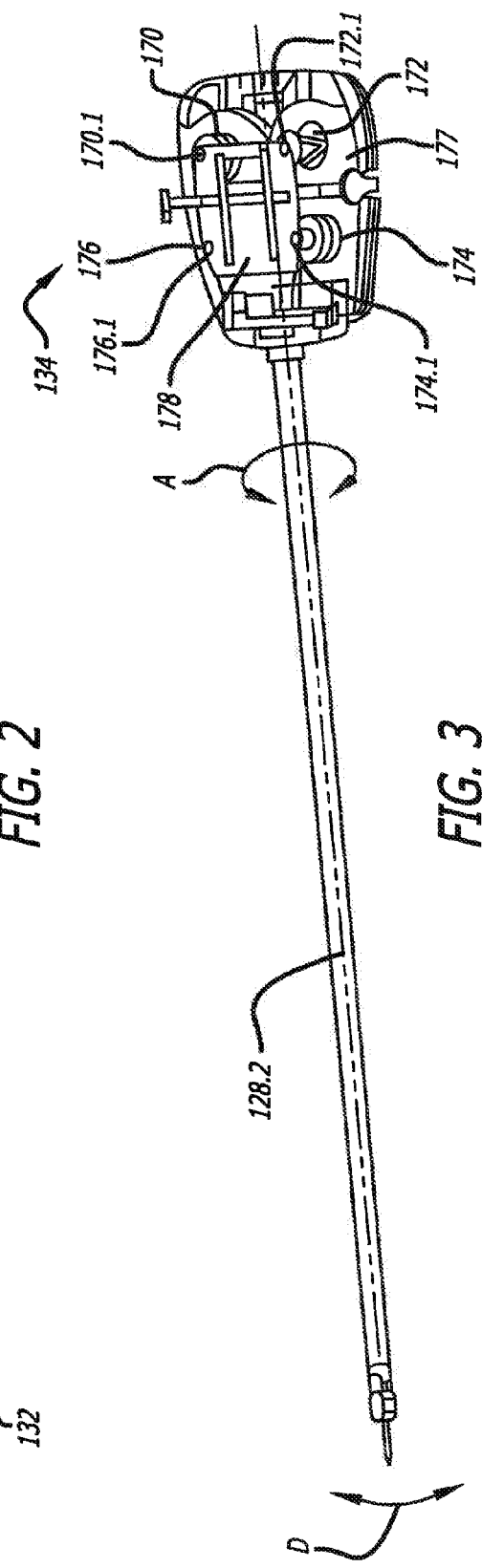
FIG. 2
FIG. 3

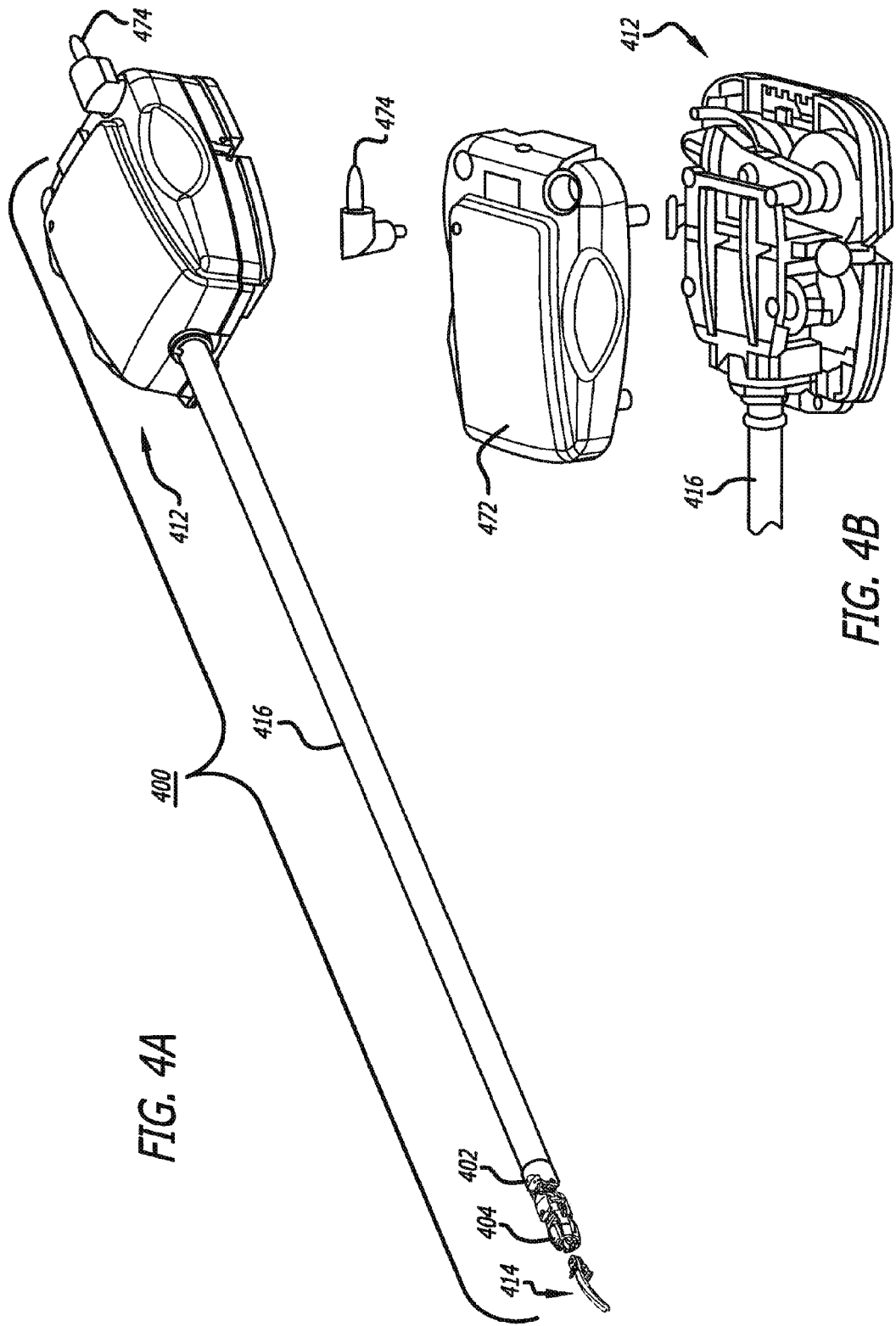

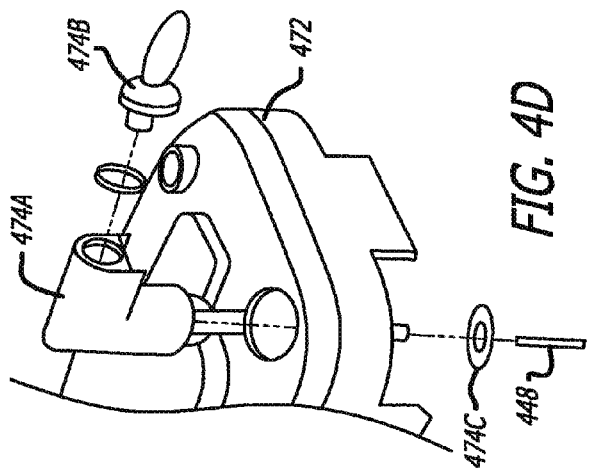
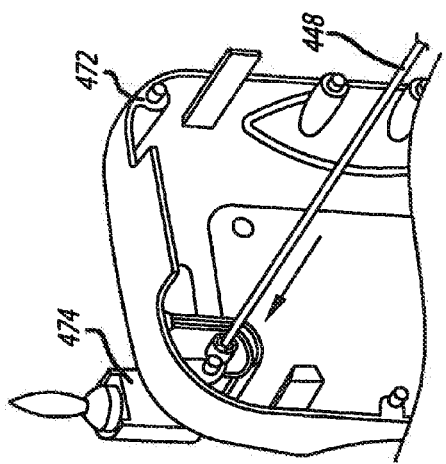
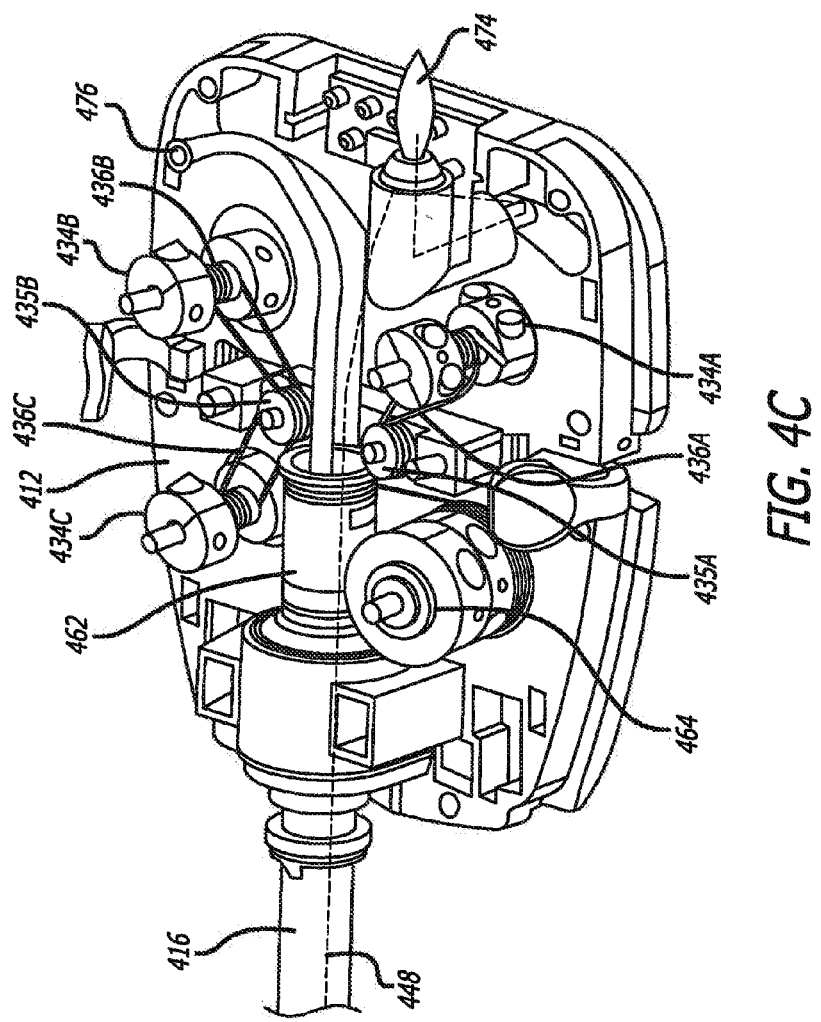
FIG. 4D
FIG. 4E
FIG. 4C

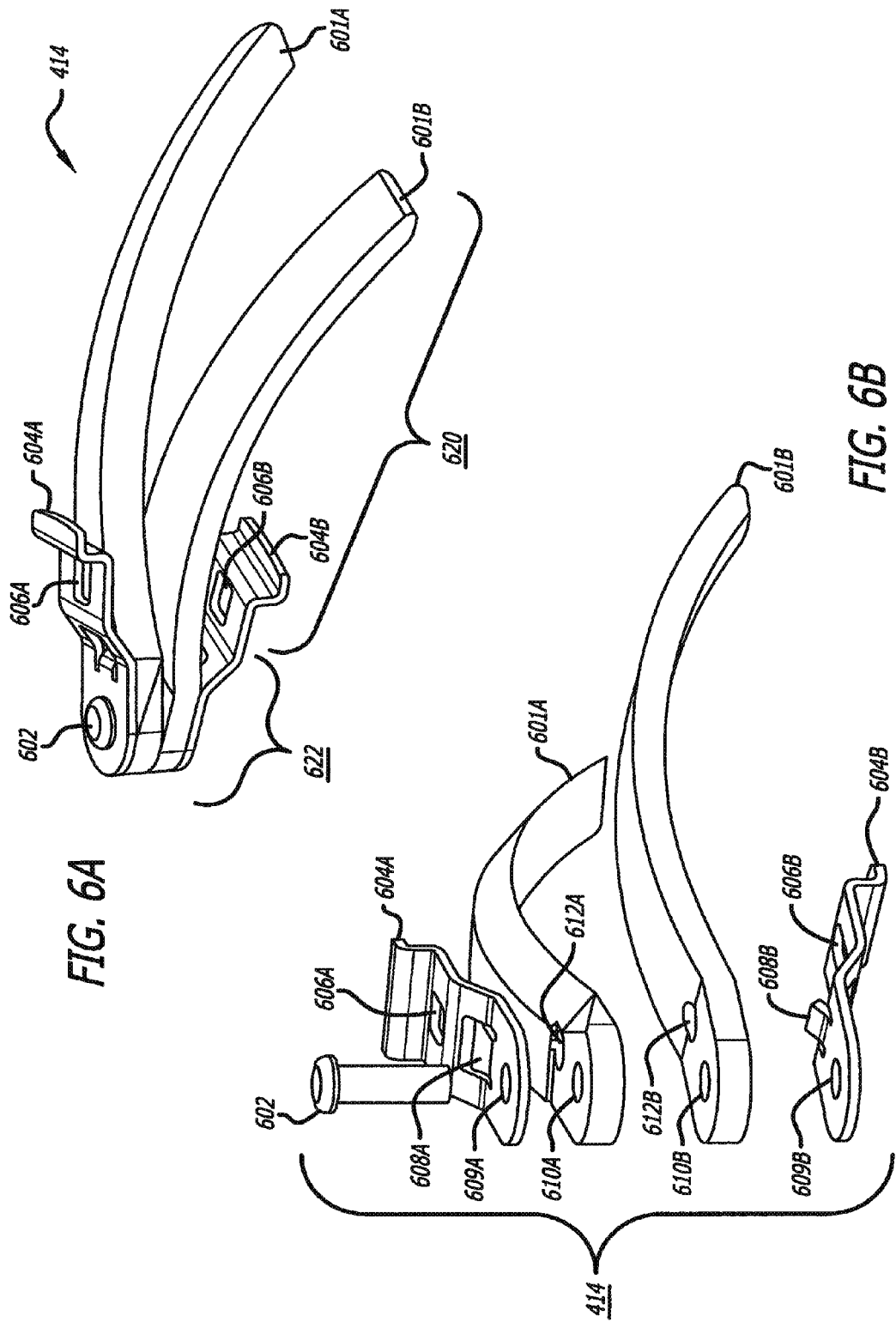

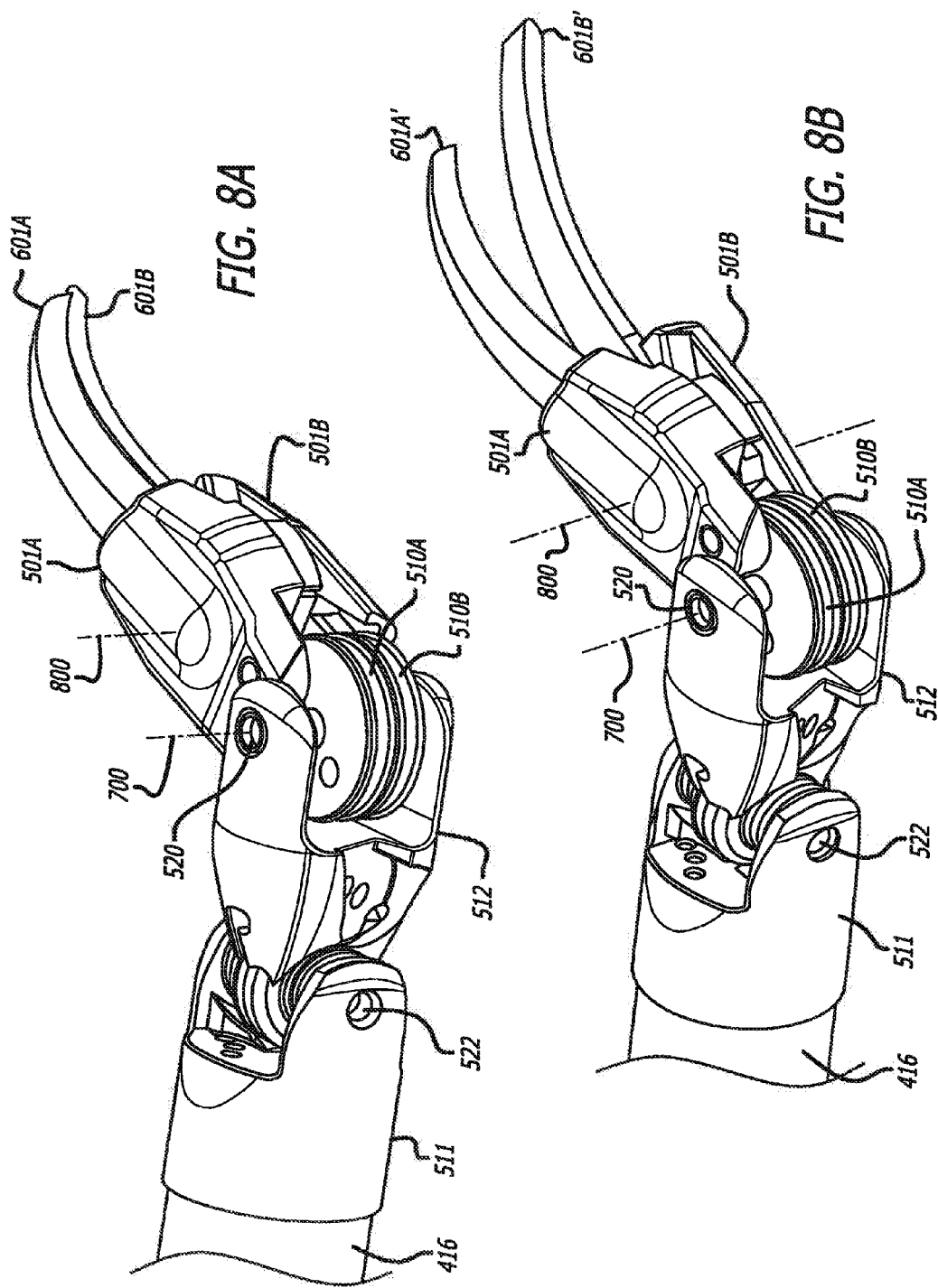

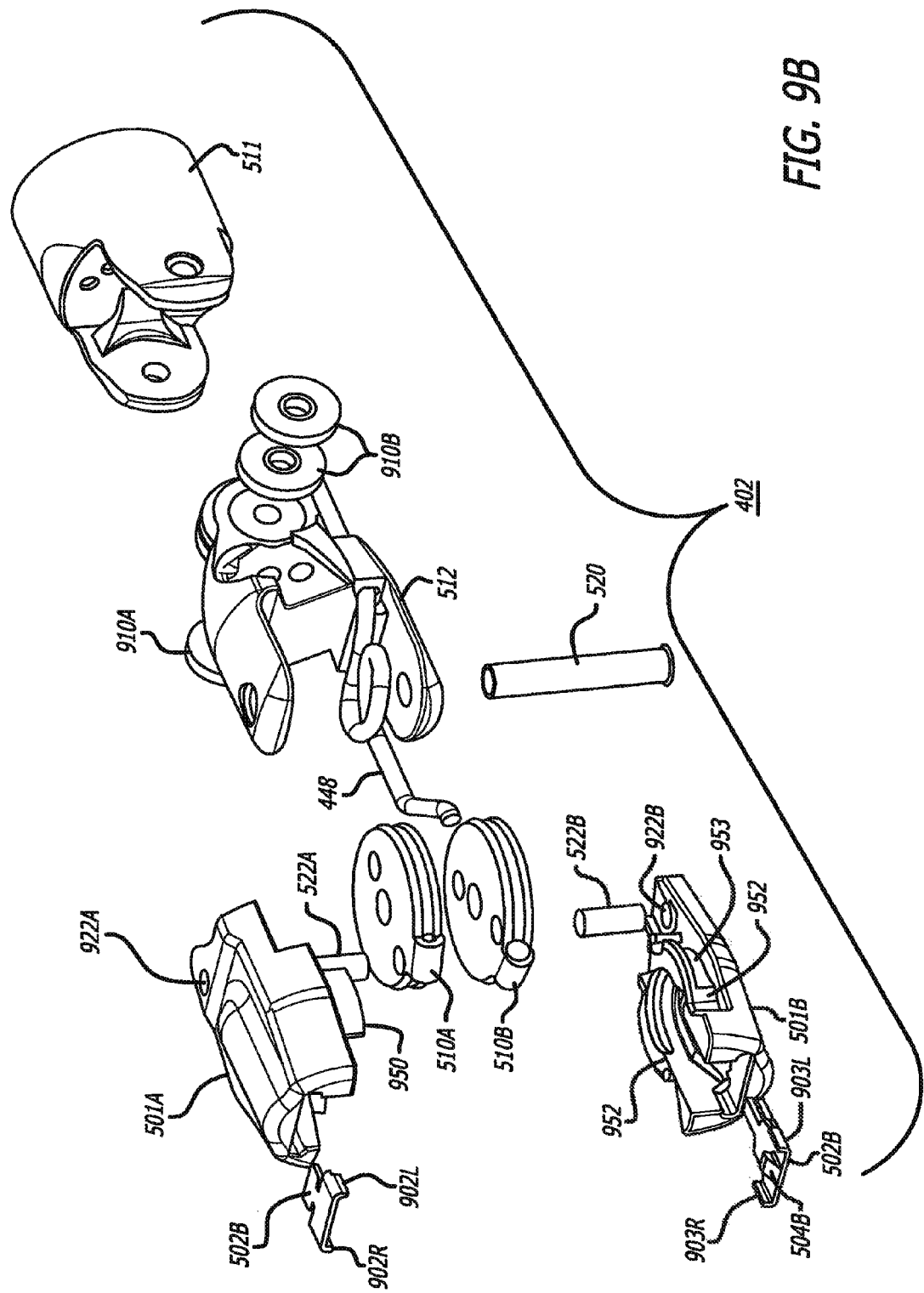

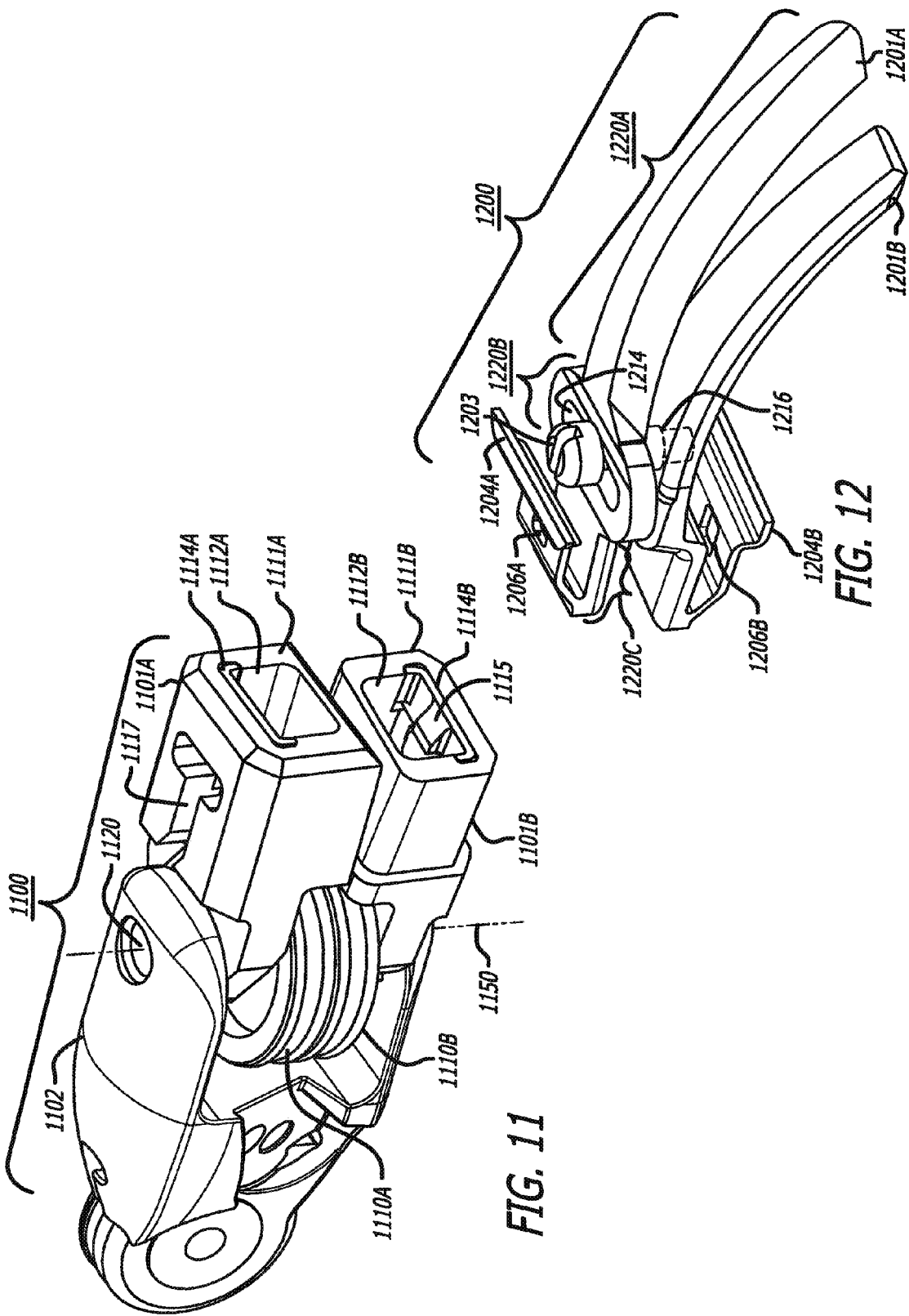

ROBOTIC SURGICAL TOOL FOR PLUGGABLE END-EFFECTORS

CROSS-REFERENCE TO RELATED APPLICATIONS

This non-provisional United States (U.S.) patent application claims the benefit of and is a divisional of U.S. patent application Ser. No. 11/238,698 filed on Sep. 28, 2005 by inventor Scott Manzo, entitled WRISTED ROBOTIC SURGICAL TOOL FOR PLUGGABLE END-EFFECTORS, now issued as U.S. Pat. No. 8,398,634 which is a continuation in part of U.S. patent application Ser. No. 10/126,451 filed on Apr. 18, 2002 by inventors Scott Manzo, entitled "ROBOTIC TOOL WITH MONOPOLAR ELECTRO-SURGICAL SCISSORS", now issued as U.S. Pat. No. 6,994,708, the full disclosure of which is incorporated herein by reference, and further claims the benefit of and is a continuation in part of U.S. patent application Ser. No. 10/611,411 filed on Jun. 30, 2003 by inventors Scott Manzo, et al., entitled "ELECTROSURGICAL INSTRUMENT WITH REPLACEABLE END EFFECTORS AND INHIBITED SURFACE CONDUCTION", now issued as U.S. Pat. No. 7,367,973, the full disclosure of which is also incorporated herein by reference; and this application further claims the benefit of U.S. Provisional Patent Application No. 60/617,341 entitled "ROBOTIC TOOL WITH WRISTED MONOPOLAR ELECTROSURGICAL SCISSORS" filed on Oct. 8, 2004 by inventor Scott Manzo, et al., the full disclosure of which is incorporated herein by reference.

Additionally, this non-provisional U.S. patent application is related to U.S. patent application Ser. No. 11/238,794 filed on Sep. 28, 2005 by inventor Scott Manzo, et al., entitled "WRISTED ROBOTIC SURGICAL TOOL WITH REPLACEABLE END EFFECTOR CARTRIDGES", pending; and U.S. patent application Ser. No. 11/094,639 filed on Mar. 30, 2005 by inventors Scott Manzo, et al., entitled "ROBOTIC TOOL WITH WRISTED MONOPOLAR ELECTROSURGICAL END EFFECTORS", now issued as U.S. Pat. No. 7,824,401.

FIELD

The embodiments of the invention are generally related to surgical instruments or tools. More particularly, the embodiments of the invention relate to robotic surgical instruments and systems that include electrosurgical end effectors and methods of performing a robotic surgical procedure.

BACKGROUND

After surgery on a patient, durable surgical instruments may generally be replaced, if inexpensive, or sterilized and repaired for reuse in another surgical procedure, if expensive. For example, a cutting blade of a metal scalpel or surgical knife may become dull after completion of a surgery. Instead of repairing and sterilizing the dull scalpel, a hospital may replace it with a new metal scalpel. Generally manual surgical instruments are less expensive and may be subject to replacement than more automated surgical equipment used in surgery, such as a laparoscope for example.

To make the more expensive automated surgical equipment more attractive for use in more hospitals, it is desirable to reduce the maintenance and replacement costs of the more automated surgical equipment after surgery.

BRIEF SUMMARY

The embodiments of the invention are summarized by the claims that follow below.

BRIEF DESCRIPTIONS OF THE DRAWINGS

FIG. 2 is a perspective illustration of a robotic surgical tool that may be used with the robotic surgical system of FIG. 1.

FIG. 3 is a perspective illustration of the robotic surgical tool in FIG. 2, with a cover of a tool base removed to show internal structures of the tool base.

FIGS. 4A-4E illustrate an exemplary electro-surgical instrument or tool with a replaceable end effectors.

FIGS. 6A-6B are magnified perspective and exploded views of the end effector cartridge illustrated in FIG. 5.

FIGS. 8A-8B illustrate opening and closing of the end effectors without moving the receptacle and end effector cartridge.

Figure 5:
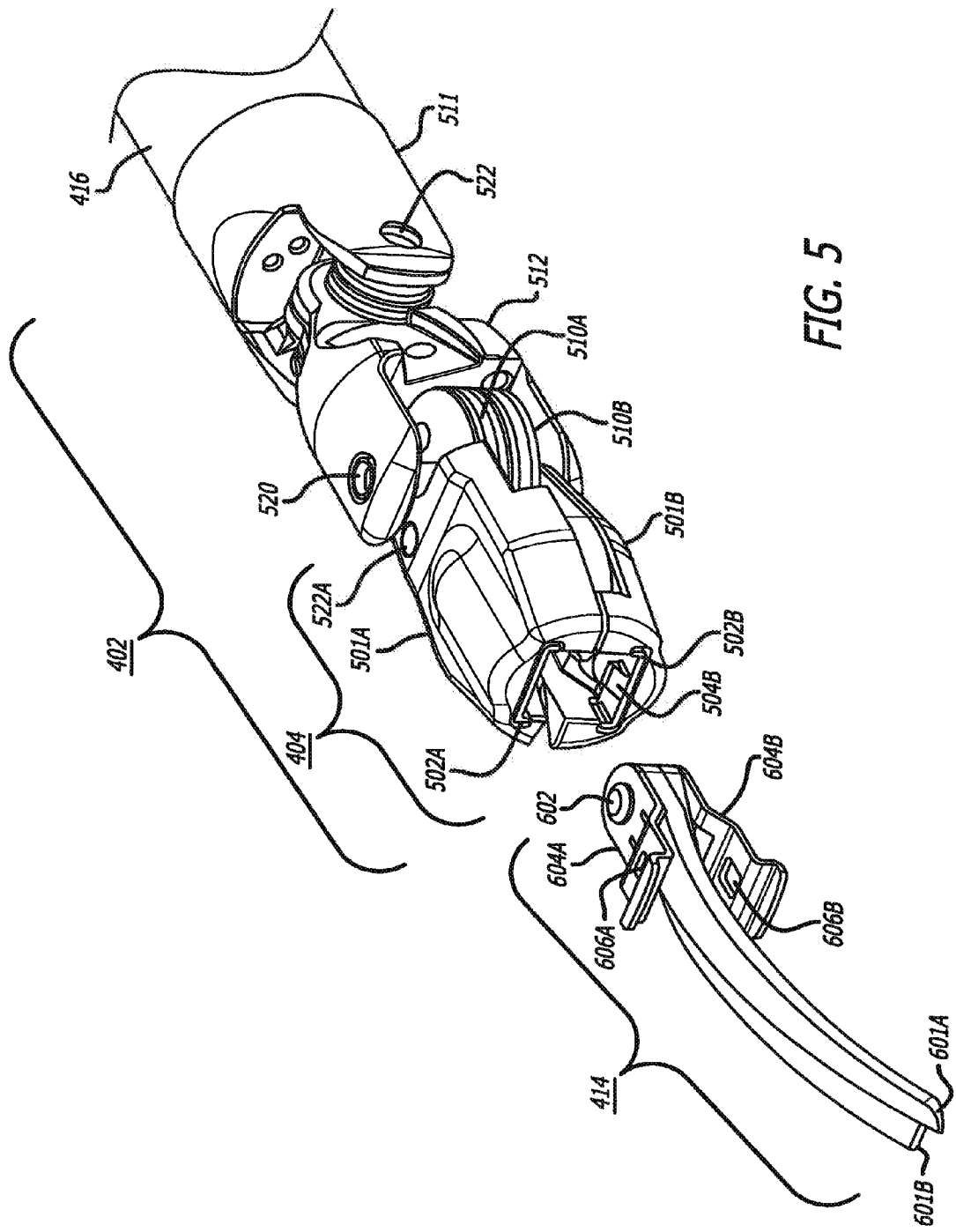
FIG. 5 is a magnified view of an end of the robotic electro-surgical tool illustrated in FIG. 4A.
Figure 9A:
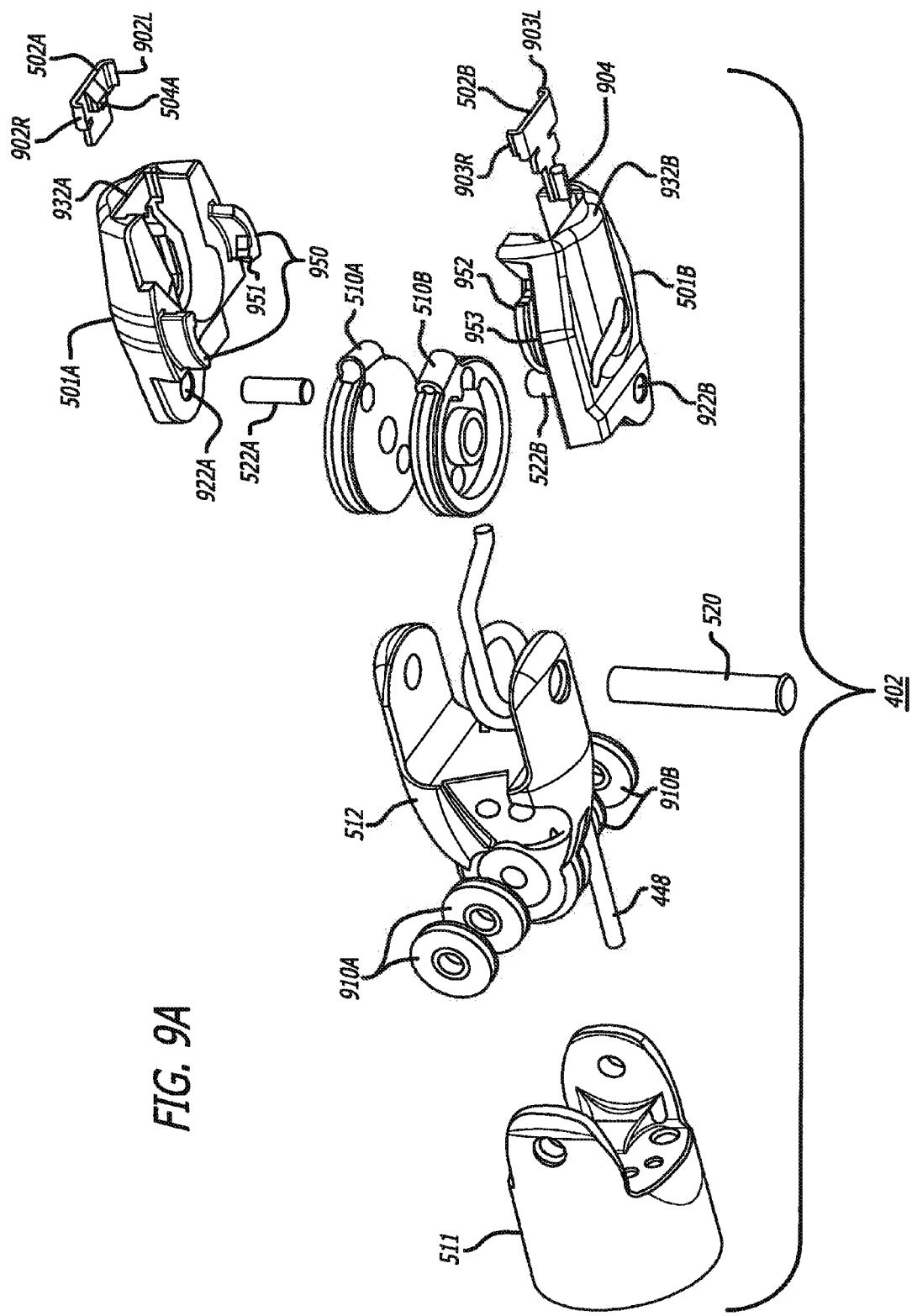

FIGS. 9A-9B illustrated magnified exploded views of the mechanical wrist of FIG. 5.

Figure 10:
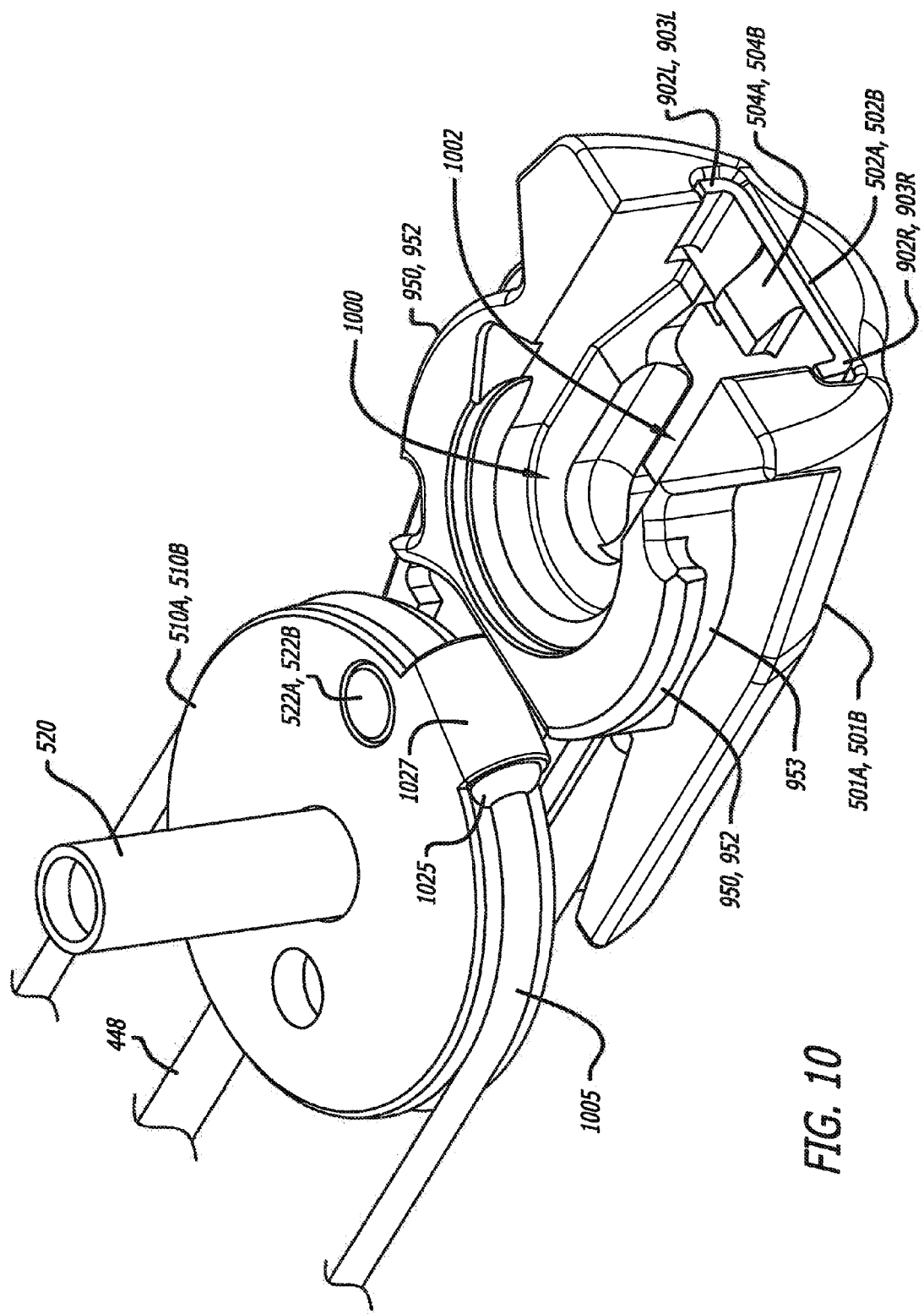

FIG. 10 illustrated a magnified view of a subassembly of the mechanical wrist of FIG. 5.

FIG. 11 illustrates a magnified view of a portion of a mechanical wrist with wristed receptacles.

FIG. 12 is a magnified perspective view of the pluggable end effector cartridge for the wristed receptacles of FIG. 11.

Figure 13:
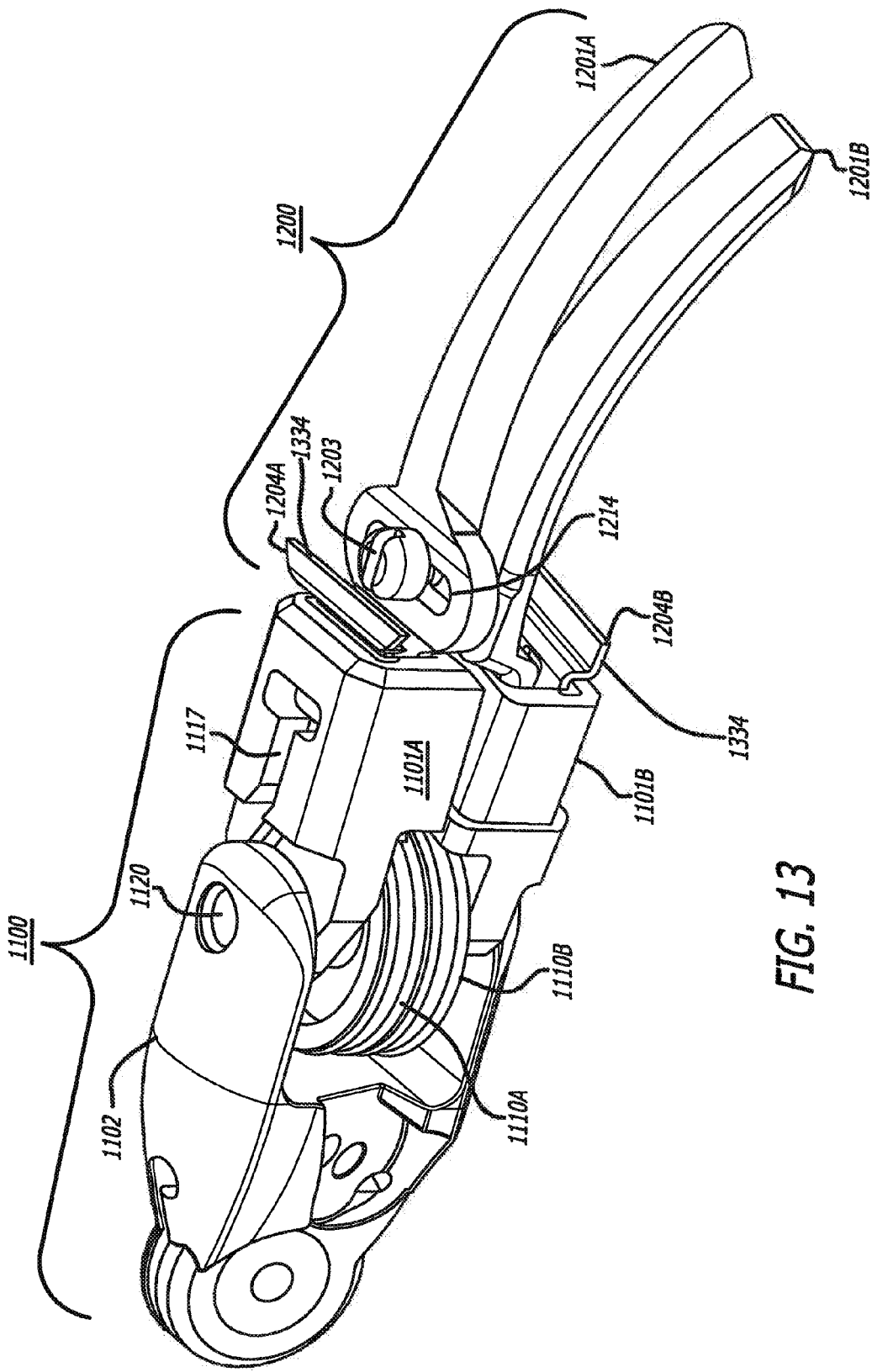

FIG. 13 is a magnified perspective view of the pluggable end effector cartridge plugged into the wristed receptacles of the mechanical wrist illustrated in FIG. 11.

Figure 14:
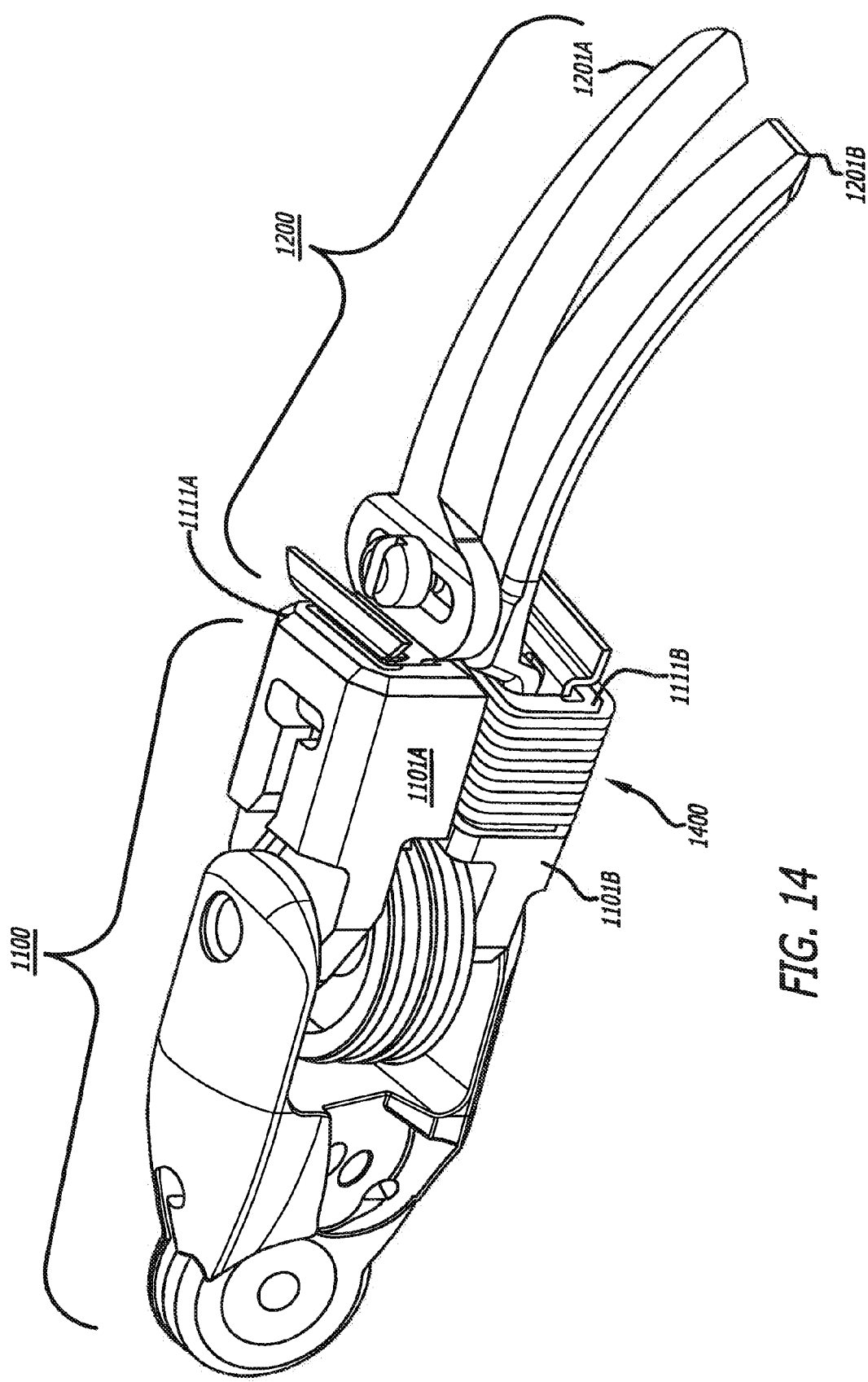

FIG. 14 is a magnified perspective view of the wristed receptacles of the mechanical wrist including additional optional electrical isolation from the pluggable end effector cartridge.

DETAILED DESCRIPTION

In the following detailed description of the embodiments of the invention, numerous specific details are set forth in order to provide a thorough understanding of the invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention provide methods, apparatus and systems for replaceable electrosurgical end effectors in robotically controlled minimally invasive surgical operations. In particular, electrosurgical cutting/shearing instruments and systems, as well as methods of performing minimally invasive robotic surgical procedures with such instruments are provided. The instruments of the embodiments of the invention are capable of treating tissue with heat produced by electrical energy while cutting, shearing, grasping, engaging, or contacting treatment tissue. The electrosurgical treatment may further reduce bleeding of tissue by cauterizing tissue and coagulating blood, or achieve various other desired effects on the treatment tissue. The electrosurgical treatment is carried out in a safe and effective manner that incorporates a variety of safety features to prevent current leakage to non-target tissue so as to reduce collateral tissue damage, unwanted burning, or the like.

Figure 1:
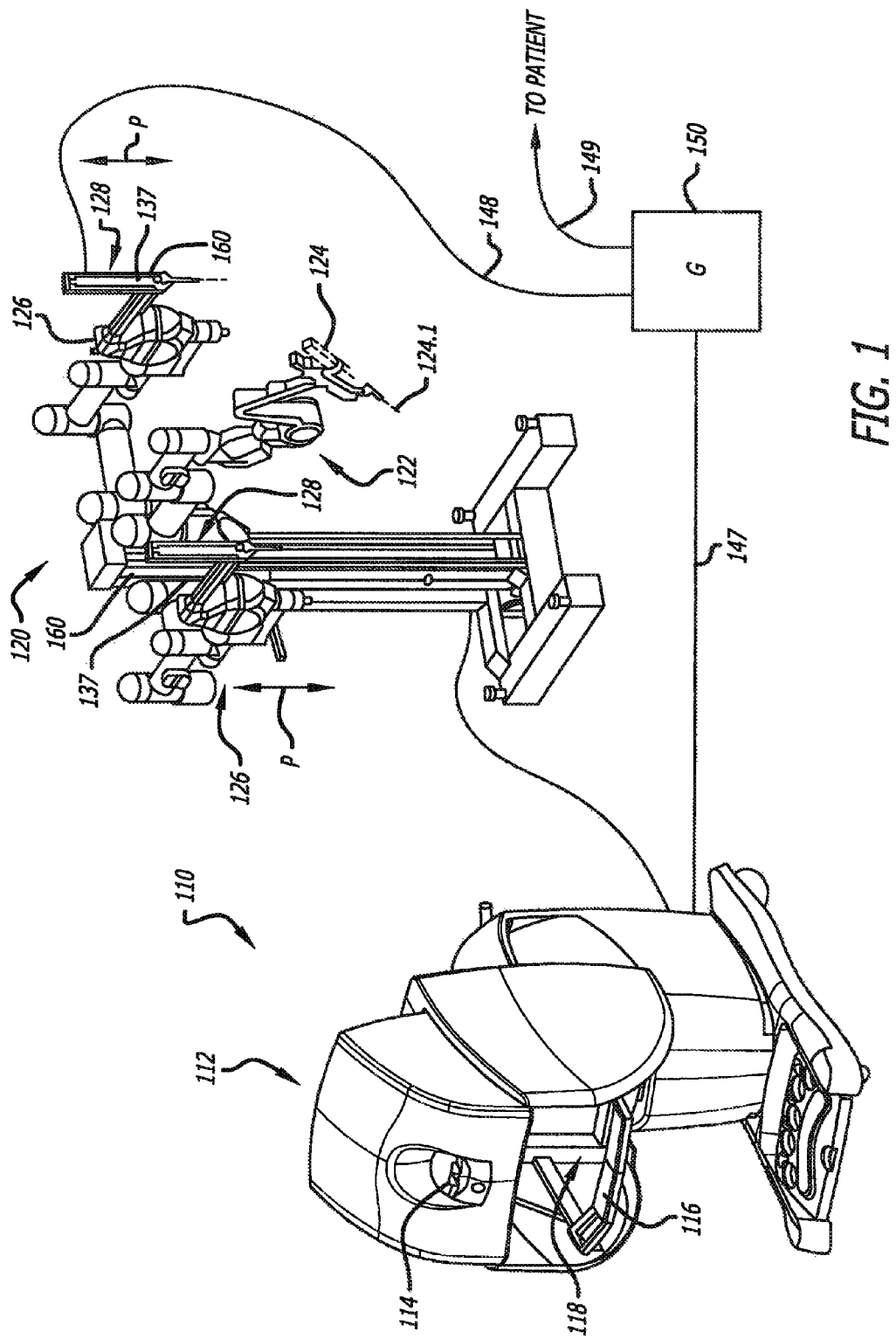
FIG. 1 is a perspective illustration of a robotic surgical system with which various embodiments of the invention may be used.

Referring now to FIG. 1, a robotic surgical system 110 generally includes a user-operated control station or "surgeons console" 112 and a surgical work station or "cart" 120. The control station 112 includes an image display module 114 for displaying an image of a surgical site, a support 116 on which an operator may rest his/her forearms, and a space 118 where two master control devices are located (not shown). When using control station 112, a surgeon or other user typically sits in a chair in front of control station 112, views the surgical site through the display module 114, and grips the master controls one in each hand while resting the forearms on support 116. An exemplary robotic surgical system as described in FIG. 1 is the DA VINCI™ system available from Intuitive Surgical, Inc. of Mountain View, Calif.

Control station 112 is generally coupled to cart 120 such that commands from the master controls may be transmitted to the cart 120. In use, cart 120 is positioned adjacent a patient requiring surgery and is then normally caused to remain stationary until a surgical procedure to be performed by means of surgical system 110 has been completed. Cart 120 typically has wheels or castors to render it mobile. Control station 112 is typically positioned remote from cart 120 and in some embodiments may be separated from cart 120 by a great distance, for example miles away, but will typically be used within an operating room with the cart 120.

In various embodiments, cart 120 includes at least three robotic arm assemblies 122, 126, 126, one of which is configured to hold an image capture device 124 and the others of which are configured to hold surgical instruments 128. Alternatively, the cart may include more or fewer than three robotic arm assemblies and the robotic arm assemblies may be configured to hold any suitable tool, instrument, imaging device and/or the like. Image capture device 124 may include any suitable device, such as an endoscope, fiber optic camera, or the like. Image capture device 124 generally includes an object viewing end 124.1 at a remote end of an elongate shaft configured to enable the viewing end 124.1 to be inserted through an entry port in a patient's body to capture an image of the surgical site.

Coupling of cart 120 to control station 112 generally enables display module 114 to display an image captured by image capture device 124. Coupling of cart 120 to control station 112 also typically allows each of the master controls on the control station 112 (not shown) to control one robotic arm assembly 126 and one surgical instrument 128. In various embodiments, each master control may alternatively be used to control more than one robotic arm assembly 126 and/or more than one surgical instrument 128.

Surgical instruments 128 on the robotic arm assemblies 126 typically include elongate shafts, with proximal and distal ends. End effectors are generally mounted on wrist-like mechanisms pivotally mounted on the distal ends of the shafts, for enabling the instruments 128 to perform one or more surgical tasks. Generally, the elongate shafts of surgical instruments 128 allow the end effectors to be inserted through entry ports in a patient's body so as to access the internal surgical site. Movement of the end effectors is generally controlled via master controls on the control center 112.

Referring now to FIG. 2, surgical instrument 128 generally includes an elongate shaft 128.1 having a proximal end 133 and a distal end 131, a pivot 132, an end effector 138 disposed at the distal end, and an instrument base 134 disposed at the proximal end. Base 134 is generally configured to releasably engage an interface member of the robotic surgical system, such as robotic surgical system 110 in FIG. 1. In general, instrument 128 is engaged with the system via base 134 (base not shown in FIG. 1) such that instrument 128 is releasably mountable on a carriage 137 which can be driven to translate along a linear guide formation 160 of the arm 126 in the direction of arrows P.

With reference to FIGS. 2 and 3, shaft 128.1 is rotatably mounted on base 134 for rotation about an axis 128.2 extending longitudinally along the shaft 128.1 as indicated by the arrows A. Thus, when mounted on an arm assembly 126, end effector 138 may have a plurality of degrees of freedom of movement relative to manipulator arm 126, in addition to actuation movement of the end effector itself. The instrument may be translated along an insertion axis (Arrows P in FIG. 1). Typically, the instrument degrees of freedom include rotation about the axis 128.2 as indicated by arrows A, and in the case of instruments 128 including pivots 132, angular displacement as a whole about pivot 132 as indicated by arrows D. Alternatively, the distal pivoting degree of freedom may be omitted. A single pivot wrist, a multi-pivot wrist, a distal roll joint mechanism, or other joints or wrist-like mechanisms may be included to provide additional operational degrees of freedom to the end effector. Movement of end effector 138 relative to manipulator arm 126 controlled by appropriately positioned actuators, such as electric motors, or the like, which respond to inputs from an associated master control at the control station 112, so as to drive the end effector 138 to a required orientation as dictated by movement of the associated master control.

Referring now to FIG. 3, base 134 of surgical instrument 128 suitably includes transmission members 170, 172, 174, and 176, which include spools secured on shafts 170.1, 172.1, 174.1, and 176.1. Ends of shafts 170.1, 172.1, 174.1, 176.1 generally extend from a side 177 of base 134 to a mounting plate 178 within base 134 and are configured to rotate. Generally, the ends of shafts 170.1, 172.1, 174.1, 176.1 at side 177 of base 134 extend through side 177, to an outer surface of side 177 (not shown). At the outer surface, each shaft 170.1, 172.1, 174.1, 176.1 includes an engaging member (not shown) configured to releasably couple with a complementary engaging member (not shown) rotatably mounted on the carriage 137 of a robotic arm assembly 126 (see FIG. 1). The engaging members on carriage 137 are generally coupled to actuators (not shown), such as electric motors or the like, to cause selective angular displacement of each engaging member on the carriage 137 in response to actuation of its associated actuator. Thus, selective actuation of the actuators is transmitted through the engaging members on the carriage 137, to the engaging members on the opposed ends of the shafts 170.1, 172.1, 174.1, 176.1 to cause selective angular displacement of the spools 170, 172, 174, 176. Where more or fewer degrees of freedom are desired, the number of spools may be decreased or increased.

Electrosurgical Tool with Replaceable End Effectors

FIGS. 4A-4E illustrate one embodiment of a robotic electrosurgical tool 400 including disposable, replaceable, or pluggable end effectors. These figures are for illustration purposes and do not necessarily reflect the actual shape, size, or dimensions of the robotic electrosurgical instrument or tool nor the disposable, replaceable, or pluggable end effector cartridge.

Referring now to FIGS. 4A-4C, the robotic electro surgical tool 400 includes a set of disposable, replaceable, or pluggable end effectors as part of a cartridge 414 for use with the minimally invasive robotic surgical system of FIG. 1 is illustrated. The end effector cartridge 414 is replaceable so that it can be readily cleaned and/or replaced when dull by fresh sharp end effectors. That is, the set of end effectors of the cartridge 414 can be plugged into and unplugged from the robotic electrosurgical tool 400.

The robotic electrosurgical tool 400 includes an elongated shaft 416 having a proximal end and a distal end; disposable replaceable, pluggable end effector cartridge 414; and an interface or tool base 412 coupled to the proximal end of the shaft 416 and removably connectable to the robotic surgical system.

At the distal end of the shaft 416 is a mechanical wrist 402 with two receptacles or two receptacle halves 404. The orientation of the mechanical wrist 402 is controlled through pulleys in the tool base 412 and the wrist 402 with cables of cable loops wrapped around each being routed through the shaft 416. The robotic system causes the pulleys in the tool base 412 to be rotated in order to control the position of the mechanical wrist 402, the receptacles or receptacle halves 404, and the end effectors 414 coupled into the receptacle. Thus, the cable of the cable loops may also be referred to as a control cable.

Further details of mechanical wrists that may be applicable to the mechanical wrist 402 are described in U.S. patent Nos. with filing dates and named inventor as follows U.S. Pat. No. 5,792,135, May 16, 1997, Madhani et al; U.S. Pat. No. 5,979,900, May 16, 1997, Madhani et al; U.S. Pat. No. 5,807,377, May 16, 1997, Madhani et al; U.S. Pat. No. 6,206,903, Oct. 8, 1999, Ramans; U.S. Pat. No. 6,312,435, Oct. 8, 1999, Wallace et al.; U.S. Pat. No. 6,371,952, Jun. 28, 1999, Madhani et al; U.S. Pat. No. 6,394,998, Sep. 17, 1999, Wallace et al.; U.S. Pat. No. 6,676,684, Sep. 4, 2001, Morley et al.; U.S. Pat. No. 6,685,698, Jan. 10, 2003, Morley et al.; U.S. Pat. No. 6,699,235, Mar. 2, 2004, Wallace et al.; U.S. Pat. No. 6,746,443, Jul. 27, 2000, Morley et al.; U.S. Pat. No. 6,817,974, Jun. 28, 2002, Cooper et al.; and application Ser. No. 10/726,795, Pub. No.: US 2004/0138700 A1, Dec. 2, 2003, Cooper et al., all of which are incorporated herein by reference.

The receptacles or receptacle halves 404 receive the disposable, replaceable, or pluggable end effectors 414 and includes a pair of actuators to actuate the pair of end effectors. In the parent patent application, U.S. patent application Ser. No. 10/126,451, the end effectors were actuated by the mechanical movement of a rod within the shaft from the interface or tool base. In contrast, the end effectors 414 in this case are actuated from the tool base 412 through a cable loop, pulleys, and a spool similar to how other elements of the wrist 402 are controlled. In this case, two cable loops are used to actuate the end effectors 414, one cable loop for each. In the parent patent application, U.S. patent application Ser. No. 10/126,451, the end effector may have been replaceable but did not move. In this case, the end effectors are moveable as well as being replaceable, disposable, or pluggable.

The disposable, replaceable, or pluggable end effectors in the cartridge 414 are used in performing a surgical operation such as cutting, shearing, grasping, engaging, or contacting tissue adjacent a surgical site. Preferably, in one embodiment of the invention, the end effector cartridge 414 includes a pair of scissor-like blades (see blades 601A-601B illustrated in FIGS. 6A-6B, for example) for cooperatively shearing the tissue. Additionally, a conductor electrically communicating with at least one blade delivers electrical energy to tissue engaged by the blades.

As shown in FIG. 4B, the tool base 412 may be enclosed by a cover 472 which mounts an electrical connector 474 for the conductor to permit connection to an electrosurgical generator G 150 illustrated in FIG. 1.

Referring momentarily back to FIG. 1, the electrosurgical generator G 150 is a part of the robotic surgical system 110. The electrosurgical generator G 150 is controlled through the control station 112 over the control cable 147 by a surgeon operating the control station. One or more wires are routed within a cable 148 that is coupled to the electrical connector 474. In the case of a monopolar system, one wire is routed within the cable 148 to the electrical connector 474 and a ground wire 149 is coupled to the patient. In the case of a bipolar system, two wires are routed within the cable 148 to the electrical connector 474 and the ground wire 149 is not used.

Referring now to FIG. 4C, an insulated conductor 448 passes out from the shaft 416 to the rear of base 412 to the electrical connector 474 for connection to the electrosurgical generator G 150.

As discussed previously, the end effectors in the cartridge 414 are actuated from the tool base 412 through a cable of a cable loop, pulleys, and a spool. The tool base 412 includes spools 434A-434C, guide pulleys 435A-435B, and cable loops 436A-436C to control the mechanical wrist 402 and the end effectors of the replaceable end effector cartridge 414.

A cable loop is a single cable routed in a loop around the drive pulley from the spool in the tool base. A cable loop may be formed by joining or splicing different segments of cable together. The cables of the cable loops 436A-434C are routed from the spools over the guide pulleys 435A-435B and through the shaft 416 to drive pulleys in the wrist 402. The tool base 412 further includes a spool 464 and a drum 462 with a cable loop coupled there-between to control the rotation of the shaft 416 and the wrist 402.

A first end of the cable of each cable loop is wrapped in one direction around the spool with the second end of the cable wrapped in an opposite direction around the same spool. In this manner, one end of cable is taken up while the other end of the cable is released during the rotation of a spool. Each spool includes a tension mechanism to avoid slack in the cable of each cable loop.

The shaft of each spool extends through the tool base 412 to its underside to couple to an engaging member. The engaging member can releasably couple to a complimentary engaging member that is in turn coupled to an actuator of the surgical system, such as an electric motor, to cause an angular displacement in the spool in response to a control signal from the control console.

An optional flush tube 476 may be mounted to a tool base cover 472 by a flush port 478 and the assembled base 412. The flush tube preferably extends forward (distally) within the base 412 to communicate with the shaft 416 to permit fluids to be passed through the shaft 416 and/or to pressurize the shaft 416. For example, introduction of insufflation gas during surgery or the introduction of cleaning or sterilization gases or fluids prior and/or subsequent to surgery may be passed to the shaft 416 via flush tube 476. U.S. Pat. No. 6,004,509 describes the use of fluids and gases to maintain sterility of a surgical instrument, and is incorporated herein by reference.

Referring now to FIGS. 4D and 4E, the base cover 472 mounts an electrical connector 474, in this case banana clip assembly 474a, 474b, and 474c, for the insulated conductor 448 to permit connection to the electrosurgical generator G 150. Note that the connections described above provide an insulated continuous electrical path from the base connector 474 to the end effectors 601A-601B, protected from tissue contact except at the jaw portions thereof. Energization of the end effectors 601A-601B is controllable by the surgeon.

Replaceable End Effector Cartridge

Referring now to FIGS. 5 and 6A-6B, the disposable, replaceable, or pluggable end effector cartridge 414 can be mounted into a receptacle 404 at the distal end of the shaft 416, as previously discussed. The disposable, replaceable, or pluggable end effector cartridge 414 can also be dismounted from the receptacle 404 so that it can be replaced with a new end effector cartridge 414.

In one embodiment of the invention, the disposable, replaceable, or pluggable end effector cartridge 414 may include two movable end effectors 601A-601B; a pivot fastener such as a pivot pin, bolt (with or without a nut), screw, or rivet 602; a first spring latch 604A; and a second spring latch 604B, coupled together as shown in FIGS. 5 and 6A. The pivot fastener 602 provides a free floating blade pivot. Drive pulleys in the mechanical wrist 402 may pull in opposite directions to pull open the moveable end effectors 601A-601B and push in opposite directions to push close the moveable end effectors 601A-601B.

The components of the set of replaceable end effectors 414 are formed of metal, an alloy, or other metalized or conductive material so that they can become electrically live and carry a current to tissue from the generator 150. In contrast, but for the electrical contacts 502A-502B, the receptacle 404 is formed of insulative materials so that the mechanical wrist 402, shaft 416, and tool base are electrically isolated from the electrically live end effector cartridge 414.

Each of the end effectors 601A-601B includes a jaw region 620 and a base region 622. In the base region 622, the end effectors 601A-601B include openings 610A-610B where the pivot pin 602 rotatably couples them together at a pivot point. In the base region 622 of each end effectors 601A-601B, is a drive opening 612A-612B along a radius from the pivot pin openings 610A-610B. The drive opening 612A-612B engages with a respective drive tab to move the end effectors 601A-601B.

The spring latches 604A-604B also include pivot openings 609A-609B through which the pivot pin 602 may be inserted. The spring latches 604A-604B further include the respective drive tabs 608A-608B to engage the drive openings 612A-612B in the end effectors 601A-601B. In this manner, the pivot pin 602 couples the spring latches 604A-604B to the respective end effectors 601A-601B at the pivot point. That is, the spring latch 604A is coupled to the end effector 601A and the spring latch 604B is coupled to the end effector 601B so that the pivot pin and the pivot openings allows them to pivot with respect to each.

In one embodiment of the invention, the pivot fastener is a rivet including a head and a shank coupled together. One end of the shank can be forced into an upset tail to mushroom over and rotatably hold the components of the cartridge 414 together. With the end effectors 601A-601B riveted together, they may hang free to rotate at the base pivot of the rivet.

Each of the latches 604A-604B includes a retention slot 606A-606B, respectively, to couple to catches 504A-504B in the electrical contacts 502A-502B of the receptacle 404. The spring latches 606A-606B can be flexed to release the retention slots 606A-606B from the catches or tabs 504A-504B of the electrical contacts 502A-502B in the receptacle to replace the end effector cartridge 414.

In one embodiment of the invention, the jaw portion of one or both of the movable end effectors 601A-601B includes a blade of a shear or scissors cartridge. With the blades being electrically hot through a current from the generator, the cartridge may be referred to as a hot shear cartridge. The pivot pin 602 for the blades may be a simple rivet or alternatively an adjustable screw to obtain a desired shearing action.

Figure 7A:
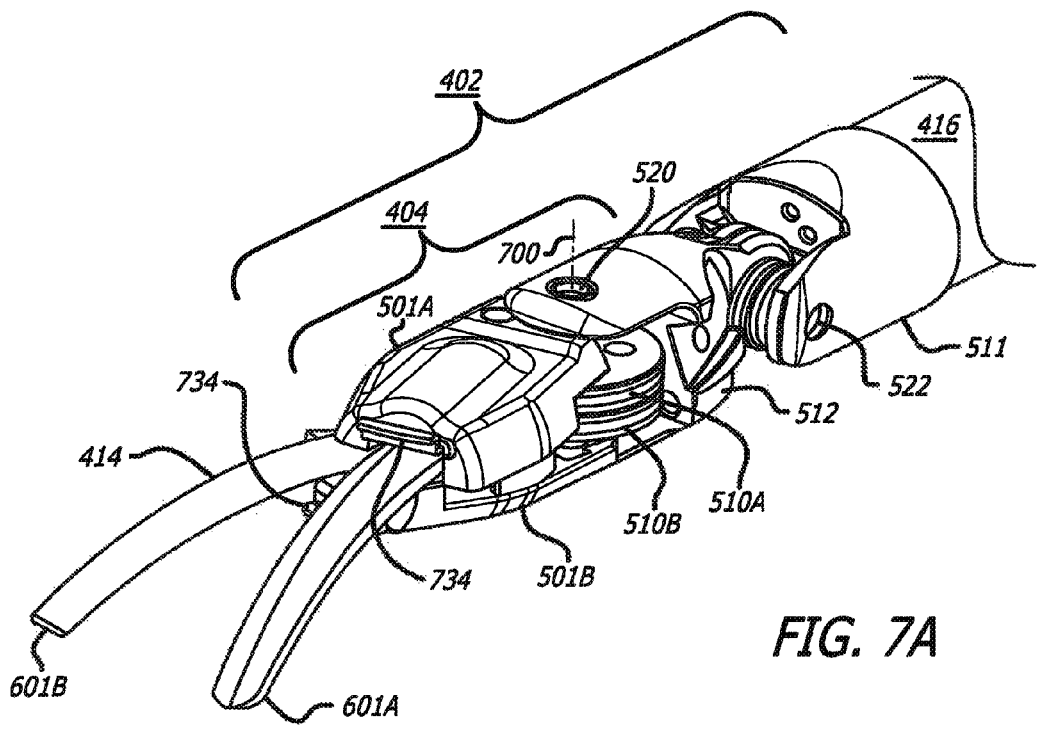
FIGS. 7A-7B illustrate movement of the receptacle and end effector cartridge while maintaining the end effectors in an open position.
Figure 7B:
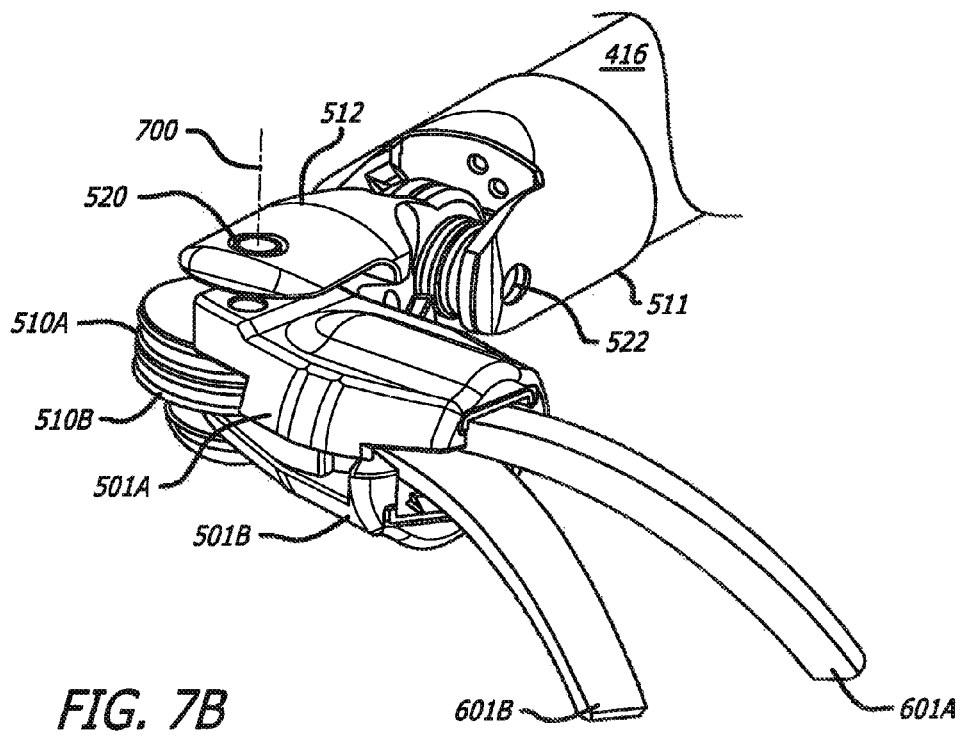

Referring now to FIGS. 7A-7B, the pluggable moveable end effector cartridge 414 is plugged into and mounted to the receptacle 404 of the mechanical wrist 402. The base region 622 of each end effector is plugged into an open end of receptacle halves 501A-501B of the receptacle 404 so that each spring latch 604A-604B is slightly flexed to allow the retention slots 606A-606B to engage with the catches 504A-504B of the electrical contacts 502A-502B. The spring latches 604A-604B snap back over the catches 504A-504B so that the retention slots 606A-606B hold the cartridge 414 coupled to the receptacle 404.

To dismount the pluggable moveable end effector cartridge 414, the spring latches 604A-604B may be squeezed together (such as with a surgical grasping tool or by use of fingers) to release the retention slots 606A-606B from the catches 504A-504B. The end effector cartridge can then be pulled out and unplugged from the receptacle halves of the receptacle.

The end effectors or blades 601A-601B preferably comprise conductive materials, such as stainless steel and the like, so as to provide a conduction path to tissue. The end effectors or blades 601A-601B may be straight or curved at the shearing surfaces thereof (e.g., curved Metzenbaum blades).

As discussed previously, the disposable, replaceable, or pluggable end effector cartridge 414 is used in performing a surgical operation such as cutting, shearing, grasping, engaging, or contacting tissue adjacent a surgical site. The end effectors 601A-601B may be blades of a shear or scissors in one embodiment of the invention. In another embodiment of the invention, the end effectors 601A-601B may be the jaws of a gripper to grasp, engage or contact tissue. The end effectors 601A-601B may take on other known surgical functions. As the pluggable moveable end effector cartridge defines the function of the robotic surgical tool, the function of the robotic surgical tool can be interchangeable with the cartridge.

Wristed Receptacle

Referring now to back to FIG. 5, the wrist 402 includes a first joint 511, a second joint 512, and the receptacle 404 coupled together. The receptacle 404 is split into two receptacle halves including a top blade driver 501A and a bottom blade driver 501B and electrical contacts 502A-502B. The receptacle 404 may also be referred to as a wristed receptacle and the blade drivers may be referred to as receptacle halves.

The top blade driver 501A is coupled to the top drive pulley 510A through the drive pin 522A. The bottom blade driver 501B is coupled to the bottom drive pulley 510B through the drive pin 522B. (see FIGS. 9B-10) The drive pulleys 510A-510B rotate about a first wrist pin 520. The top blade driver 501A and the bottom blade driver 501B are pivoted by the respective drive pulleys 510A-510B to rotate about a respective top engagement feature 950 engaged with a bottom engagement feature 952 defining an axis 800. The first joint 511 is coupled to the second joint 512 through a second wrist pin 522. The first joint 511 is coupled to the distal end of the shaft 416.

Referring now again to FIGS. 7A-7B, the pluggable moveable end effector cartridge 414 is plugged into the receptacle 404. Together, the pluggable moveable end effector cartridge 414 and the receptacle 404 can be rotated together about the axis 700 of the wrist pin 520. To accomplish this rotation, both drive pulleys 510A-510B are conjunctively controlled together through pulleys in the interface base by means of cable loops routed through the shaft 416 and into the wrist 402. That is, with no difference in control of the drive pulleys, they move in lockstep together, the end effectors are not opened or closed by the blade drivers 501A-501B. However if there is a difference in the control of the drive pulleys 510A-501B (e.g., one moves less, one doesn't move, or they move in different directions), the end effectors 601A-601B are respectively pivoted opened or closed by the blade drivers 501A-501B.

FIGS. 8A-8B illustrate how the end effectors 601A-601B are respectively moved to open and closed positions by the blade drivers 501A-501B. In FIG. 8A, the end effectors 601A-601B of the cartridge 414 are in a closed position as it may be to plug the cartridge 414 into the receptacle 404. The top blade driver 501A may be pivoted in one direction about the axis 800 while the bottom blade driver 501B is pivoted in the opposite direction about the axis 800. This causes the end effectors 601A-601B to pivot about the pivot pin 602 near the pivot axis 800 to the positions 601A' and 601B', respectively. The pivot axis 800 is offset from the axis 700 where the driver pulleys rotate. The offset axis 800 allows for increased opening and a mechanical advantage between and to the end effectors 601A-601B. Additionally, this increases the distance between the end effectors 601A-601B and the metal components of the wrist, such as the joint 512, improving electrical isolation between the two (assuming the blade drivers 501A-501B are made from an insulative plastic). That is, the drive pulleys 510A-510B coupled to the blade drivers 501A-501B are not controlled together in the same direction so that the end effectors 601A-601B may be opened and closed together. In one embodiment of the invention, one drive pulley and blade driver is moved while the other driver pulley and blade driver remain stationary in the same position. IN another embodiment of the invention, both drive pulleys and blade drivers move in opposed directions.

With additional control complexity, the driver pulleys 510A-510B and blade drivers 501A-501B can be controlled disjointly so that the end effectors 601A-601B can be moved about both axes 700 and 800 so as to be reoriented directionally (see FIGS. 7A-7B) and positionally (see FIGS. 8A-8B). This control can be readily provided by the control station 112 through the respective spools, pulleys and cable loops routed in the shaft from the tool base to the wrist 402.

Referring now to FIGS. 9A-9B, exploded views of the wrist 402 are provided to better illustrate the components thereof. The top and bottom blade drivers 501A-501B include drive pin openings 922A-922B to respectively receive the drive pins 522A-522B that are coupled to the drive pulleys 510A-510B. The top and bottom blade drivers 501A-501B further include a connector slot 932A-932B to receive the electrical connectors 502A-502B, respectively.

Additionally, the top blade driver 501A includes top engagement features 950 in its left and right shoulders and the bottom blade driver 501B includes bottom engagement features 952 in its left and right shoulders. The inner surfaces of top engagement features 950 couple to the left and right sides of the end effector 601A near its base portion. Similarly, the inner surfaces of the bottom engagement features 952 couple to the left and right sides of the end effector 601B near its base portion. The top and bottom engagement features 950,952 apply pivoting forces to the end effectors 601A,601B respectively from the drive pulleys 510A,510B.

Furthermore, the top engagement features 950 each include a nib 951 on its inner surface to engage curved slots 953 in the outer surface of each bottom engagement features 952. The nibs 951 engaged in the curved slots 953 rotatingly couple the top blade driver 501A and the bottom blade driver 501B together.

The top electrical contact 502A includes the catch 504A and left and right shoulders 902L-902R. The left and right shoulders 902L-902R couple to the edges of the spring latch 604A.

The bottom electrical contact 502B includes the catch 504B, left and right shoulders 903L-903R, and a wire connector 904. The wire connector 904 may be a crimp connector or a solder sleeve, for example, to couple the wire 448 to the electrical contact 502B. The left and right shoulders 903L-903R couple to the edges of the spring latch 604B.

The wire 448 is carefully routed through the wrist wrapping around the wrist pin 520 so that it can pivot with the receptacle and avoid damage. The wrist 402 includes idle pulley pairs 910A-910B so that the control cables of the cable loops can be routed through the wrist to the drive pulleys 510A-510B.

Referring now to FIG. 10, a magnified view of a wrist subassembly is illustrated including a blade driver 501A, 501B; drive pin 522A,522B; drive pulley 510A,510B; wrist pin 520; and electrical wire 448 assembled together. The drive pulley 510A,510B is mounted over the wrist pin 520 so that the drive pin 522A,522B couples the blade driver 501A,501B and pulley together.

The drive pulley 510A,510B is coupled to a control cable of a cable loop 1005 routed within the shaft from the tool base. A crimped sleeve 1025 around the cable of the cable loop 1005 fastens the cable to a boss 1027 of the drive pulley 510A,510B to couple the cable loop and the pulley together. Other cable loops may be similarly coupled to a drive pulley.

The blade driver 501A,501B includes the engagement features 950,952 around a base cavity 1000 and a pin cavity 1002. The base cavity receives the base region of the end effectors 601A-601B. The pin cavity 1002 is deeper to receive an end of the fastener 602 of the end effector cartridge 414.

The magnified view of FIG. 10 also better illustrates the catch 504A,504B and the alignment edges 902L,903L and 902R,903R of the electrical contact 502A,502B.

In one embodiment of the invention, the robotic electrosurgical tool is monopolar with one or both end-effectors 601A-601B being electrically hot with the same polarity. In this case, the patient is grounded via cable 149 in order to complete the circuit.

In another embodiment of the invention, the robotic electrosurgical tool may be bipolar with both end-effectors 601A-601B being electrically hot with differing polarity. That is, each end-effector may be wired independently to be hot such that when the same tissue is touched by each, the circuit is completed. In which case, the end effectors 601A-601B are to be electrically isolated from each other. Two insulated conductive wires 448 are routed from the tool base through the shaft and the wrist. One wire couples to the end effector 601A. The other wire couples to the end effector 601B.

The insulated conductive wire 448 is routed from the tool base through the shaft and the wrist to the wristed receptacle 404. The insulated conductive wire 448 is crimped and electrically coupled to one of the electrical contacts 502A-502B. The crimp connection 904 may be use to crimp the wire to the electrical contact. In other cases, the wire may be welded or soldered to the electrical contact 502A,502B.

As previously discussed, the components of the cartridge 414 may be formed out of a metal, alloy, or metalized material to be conductive. When the cartridge is coupled into the receptacle, the electrical contacts 502A,502B mechanically and electrically couple to the end effectors 601A,601B. That is, when the cartridge 414 is coupled into the receptacle 404, its conductive components can become electrically alive. As the end effectors are conductive they can be energized by a current flowing through the insulated conductive wire 448 from the tool base. That is, the wire 448 supplies electrical power from an electrical generator G 150 to the end effectors.

A number of components of the wristed receptacle 404 are non-conductive or insulative to avoid shorting the current in the insulated conductive wire 448 to an undesired location in a surgical site or back to the wrist 402. For example, the blade drivers 501A-501B may be formed of an insulative material such as plastic (e.g., polypropylene, or fluoropolymer). The components that are formed of insulative materials, such as plastic, are not electrically alive. The wrist 402, shaft 416, and tool base are preferably not alive as they are electrically isolated through the insulative components.

While the end effector cartridge has been described as being replaceable, in another embodiment of the invention the end effectors are not a replaceable cartridge but instead are a part of the receptacle that includes the end effectors. In this manner, the spring latches need not be provided. Manufacturing costs may be lowered in this case due to the standard components that can be used, such as the interface base, the shaft, and the wrist for the manufacture of the robotic surgical tool.

Wristed Receptacle with Receptacle Arms

In the embodiments of the replaceable end effector cartridge previously described, the end effectors were directly actuated by pulleys of the mechanical wrist and pivoted about a pivot pin of the cartridge that is offset from the wrist pin. In the embodiments of the pluggable end effector cartridge described below, the end effectors are directly actuated by pulleys and receptacles of the mechanical wrist to pivot about one main pivot point at a wrist pin.

Referring now to FIG. 11, a wristed receptacle 1100 is illustrated. The wristed receptacle 1100 couples to a first joint of the mechanical wrist that is coupled to the end of the shaft 416 of the surgical tool 400. The wristed receptacle 1100 is used in place of the receptacle 404 described previously.

The wristed receptacle 1100 includes a first receptacle arm 1101A, a second receptacle arm 1101B, a first drive pulley 1110A, a second drive pulley 1110B, and a wrist pin 1120 coupled to a second joint 1102. The first drive pulley 1110A is directly coupled to the first receptacle arm 1101A to control its position. The second drive pulley 1110B is directly coupled to the second receptacle arm 1101B to control its position. As previously discussed, a pair of drive pulleys may be jointly controlled together to actuate end effectors or move the end effectors about. In this case, the drive pulleys 1110A-1110B may be jointly controlled together to move the receptacle arms with end effectors plugged therein about a pivot point 1150 with an axis substantially concentric with the wrist pin 1120. Additionally, the drive pulleys 1110A-1110B may be separately controlled to open or close the end effectors 1201A-1201B about the pivot point 1150 with it pivot axis substantially concentric with the wrist pin 1120.

The receptacle arms 1101A-1101B include a receptacle 1111A-1111B having an opening 1112A-1112B with an electrical contact 1114A-1114B, respectively. The electrical contact 1114A-1114B is similar to the electrical contacts 502A-502B illustrated in FIG. 5 previously described. Each of the electrical contacts 1114A-1114B includes a catch 1115 that is similar to the catches or tabs 504A-504B previously described.

One or both of the receptacles 1111A-1111B may further include a pocket 1117 to receive one electrical wire 448. Each pocket 1117 may be filled with a potting compound to protect and electrically isolate the electrical wire and electrical contact. The electrical wire 448 may couple to an electrical contact 1114A-1114B by soldering, a crimp connector, or other known means of coupling a wire to a contact. The insulated wire 448 is routed from the interface base through the shaft 416 and into the wrested receptacle 1100 to couple to the metal contact 1114A or 1114B.

But for the electrical contacts 1114A-1114B, the receptacle arms 1101A-1101B are formed out of an insulated material, such as plastic, polypropylene, or fluoropolymer, in order to electrically isolate the wristed receptacle 1100 from the conductive components of the end effector cartridge 1200 that may be electrically live.

Referring to FIG. 14, the wristed receptacle 1100 may optionally include a fluor-plastic heat shrink 1400 around the plastic receptacles 1111A-1111B to provide additional electric isolation from an electrically live end effector cartridge 1200. The fluoro-plastic heat shrink 1400 may alternatively be a fluoro-polymer to provide a good insulator.

Pluggable Moveable End Effectors

Referring now to FIG. 12, a pluggable moveable end effector cartridge 1200 is illustrated. The pluggable moveable end effector cartridge 1200 includes a first pluggable moveable end effector 1201A, a second pluggable moveable end effector 1201B, and a fastener 1203 to couple the first moveable end effector and the second moveable end effector together as shown.

Each of the moveable end effectors 1201A-1201B includes a jaw portion 1220A, an off-center portion 1220B and a base portion 1220C. Near the off-center portion 1220B of each end effector, a fastener 1203 may be used to couple the end effectors together.

The first moveable end effector 1201A includes a slotted opening 1214 through which the fastener 1203 may be inserted. The second end effector 1201B includes an opening 1216 to receive the fastener 1203. The slotted opening 1214 may allow the first moveable end effector 1201A to slide over the second moveable end effector 1201B within a range of lateral movements. In one embodiment of the invention, the slotted opening is a medial lateral arc slot in one end effector 1201A to engage the fastener 1203, such as a rivet through the opening 1216 in the end effector 1201B. The fastener 1203 engaged in the slotted opening binds the jaws together in one direction along the length of the end effectors (longitudinal) and allows movement over each other in the width direction (lateral).

The axis 1150 about which the first end effector and the second end effector 1201B are pivoted is at the wrist pin 1120 of the wristed receptacle 1100. The first and second moveable end effectors 1201A-1201B do not pivot about the fastener 1203.

The fastener 1203 in one embodiment of the invention is a screw with a screw head and a threaded shaft that includes a male thread. In the case the fastener 1203 is a screw, the opening in the second moveable end effector 1201B includes a female thread into which the male thread of the screw 1203 may be threaded. Alternatively, the opening 1216 in the second moveable end effector 1201B may not be threaded. Instead, the fastener 1203 may be a bolt and nut combination, a rivet, or other known fastener inserted through the slotted opening 1214 and the opening 1216 in the respective end effectors.

In a preferred embodiment of the invention, the jaws of the end effector are scissor blades and the pluggable moveable end effector cartridge 1200 is a scissors cartridge. In which case, the fastener 1203 may be a screw to apply tension between the blades in order for them to cut tissue. The screw fastener can be also be adjusted to maintain a correct overlap in the jaw blades of the scissors cartridge to obtain a desired shearing action. In this case, the drive pulleys are directly coupled to the receptacles and can control the blades mounted therein so as to move them in opposed directions to provide a shearing action.

The end effectors 1201A-1201B further include a spring latch 1204A-1204B, respectively, that may be formed as an integral part thereof. Each of the spring latches 1204A-1204B includes a retention slot 1206A-1206B to respectively couple to the catches 1115 of the respective receptacles 1111A-1111B.

A substantial number, if not all, of components of the pluggable moveable end effector cartridge 1200 are formed out of metal, a metal alloy, a metalized material, or other conductive material to conduct electricity. In this manner, the end effector cartridge may be made electrically live by being coupled to the electrical contacts 1114A-1114B.

Referring now to FIG. 13, the cartridge 1200 is plugged into the wristed receptacle 1100. The base portion 1220C of each end effector 1201A-1201B is coupled into the respective receptacles 1111A-1111B. The retention slots 1206A-1206B are engaged over the catches 1115 in each receptacle. The spring latches 1204A-1204B are flexible and allow them to be depressed in order to have the retention slots 1206A-1206B be engaged with the catches 1115. Similarly, the spring latches 1204A-1204B extend out from the arm receptacles 1111A-1111B in order that they may be depressed to release and unplug the end effector cartridge 1201 from the wristed receptacle 1100.

Each of the spring latches 1204A-1204B is pressed inward toward the axis of the end effectors in order to release the retention slot from the catches 1115. The end effector cartridge 1200 may then be pulled out from the wristed receptacle 1100. In this manner, a dull or worn end effector cartridge may be replaced by a fresh or new end effector cartridge.

As discussed previously, the wristed receptacle 1100 couples to a first joint of the mechanical wrist that is coupled to the end of the shaft 416 of the surgical tool 400. The second joint 1102 couples between the receptacles 1101A-1101B and the first joint. The mechanical wrist may further include idle pulley pairs, idle pins, an additional wrist pin, and pulleys as described previously with reference to FIGS. 9A-9B.

Further details of the components of mechanical wrists that may be applicable with the wristed receptacle 1100 are described in U.S. patent Nos. with filing dates and named inventor as follows U.S. Pat. No. 5,792,135, May 16, 1997, Madhani et al; U.S. Pat. No. 5,979,900, May 16, 1997, Madhani et al; U.S. Pat. No. 5,807,377, May 16, 1997, Madhani et al; U.S. Pat. No. 6,206,903, Oct. 8, 1999, Ramans; U.S. Pat. No. 6,312,435, Oct. 8, 1999, Wallace et al.; U.S. Pat. No. 6,371,952, Jun. 28, 1999, Madhani et al; U.S. Pat. No. 6,394,998, Sep. 17, 1999, Wallace et al.; U.S. Pat. No. 6,676,684, Sep. 4, 2001, Morley et al.; U.S. Pat. No. 6,685,698, Jan. 10, 2003, Morley et al.; U.S. Pat. No. 6,699,235, Mar. 2, 2004, Wallace et al.; U.S. Pat. No. 6,746,443, Jul. 27, 2000, Morley et al.; U.S. Pat. No. 6,817,974, Jun. 28, 2002, Cooper et al.; and application Ser. No. 10/726,795, Pub. No.: US 2004/0138700 A1, Dec. 2, 2003, Cooper et al., all of which are incorporated herein by reference.

Generally, the cartridge design in the embodiments of the invention disclosed herein aims to keep the mechanical wrist dry. Current leakage from the instruments is minimized from areas other than the active electrode. For example, this may be accomplished by the outer tube design (e.g., materials, coatings), how the outer tube design relates to working with a metal cannula, hypotube segment lengths and locations, hypotube isolation, vectran isolation to "interrupt" a hypotube to contain current to the instrument front end (creates electrical discontinuity), a seal at the distal end of the instrument lumen to keep fluids out of the lumen, coatings on the boot, or materials on the boot. Boot durability may be maintained by material and coating selection. Additionally, scissor blades may be designed to minimize tissue sticking.

The embodiments of the invention are thus described. Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Additionally, while a mechanical wrist and various mechanisms are illustrated and described herein to actuate the end effectors, other types of mechanical wrists, as well as other mechanisms may be used to actuate the end effectors, such as the mechanical wrist and mechanism illustrated by FIGS. 37-41 and described in U.S. Pat. No. 6,817,974, filed by Cooper et al. on Jun. 28, 2002 which has been incorporated by reference herein. Therefore, the above description should not be taken as limiting the scope of the invention which is defined by the appended claims.

What is claimed is:

1. A robotic surgical tool comprising:
    a first pulley and a second pulley;
    a first receptacle coupled to the first pulley;
    a second receptacle coupled to the second pulley;
    a first end effector removably coupled to the first receptacle;
    a second end effector removably coupled to the second receptacle;
    a fastener rotatably fastening together the first and second end effectors at a first pivot axis;
    a shaft having a distal end to extend the first and second end effectors into a surgical site;
    an interface base coupled to a proximal end of the shaft, the interface base to couple to a robotic slave to control the first and second end effectors, the interface base including a first spool to control the first end effector and a second spool to control the second end effector;
    a first cable loop routed in the shaft between the first pulley and the interface base, the first cable loop coupled to the first pulley and having a first end wrapped around the first spool of the interface base in a first direction and a second end wrapped around the first spool in a second direction opposite the first direction to control the first end effector; and
    a second cable loop routed in the shaft between the second pulley and the interface base, the second cable loop coupled to the second pulley and having a first end wrapped around the second spool of the interface base in a first direction and a second end wrapped around the second spool in a second direction opposite the first direction to control the second end effector;
    wherein the first pulley and second pulley respectively rotate the first and second receptacles about a second pivot axis parallel to the first pivot axis and the first and second receptacles in turn rotate the first and second end effectors about the first pivot axis to open and close the jaws of the first and second end effectors, or to yaw the first and second end effectors together.

2. The robotic surgical tool of claim 1, wherein
the first receptacle is a first half receptacle, and
the second receptacle is a second half receptacle.

3. The robotic surgical tool of claim 2, wherein
the robotic surgical tool is an electro-surgical tool,
the first and second end effectors are formed of a conductive material and electrically coupled together,
the interface base includes an electrical connector to couple to a generator, and
the robotic surgical tool further includes
a wire having a first end coupled to the electrical connector, the wire routed down the shaft to the first or second receptacle, the wire having a second end to electrically couple to at least one of the first or second end effectors for electro-cautery.

4. The robotic surgical tool of claim 1, wherein
the robotic surgical tool is an electro-surgical tool,
the first and second end effectors are formed of a conductive material and electrically isolated from each other,
the interface base includes an electrical connector with a first terminal and a second terminal to couple to a generator, and
the robotic surgical tool further includes
a first wire having a first end coupled to the first terminal of the electrical connector,
a second wire having a first end coupled to the second terminal of the electrical connector,
wherein the first and second wires routed down the shaft to the first and second receptacles, respectively, the first wire having a second end to electrically couple to the first end effector and the second wire having a second end to electrically couple to the second end effector for electro-cautery.

5. The robotic surgical tool of claim 1, further comprising:
a mechanical wrist coupled between the first and second receptacles and the shaft, the mechanical wrist having a first joint for a first degree of freedom and a second joint for a second degree of freedom, the first joint coupled to the shaft and the second joint coupled to the first joint and the first and second receptacles.

6. The robotic surgical tool of claim 1, wherein
the first and second pulley independently rotate the first and second receptacles about the second pivot axis, such that the first and second receptacles rotate in opposite directions.

7. The robotic surgical tool of claim 1, wherein
the first and second pulley independently rotate the first and second receptacles about the second pivot axis, such that the first and second receptacles rotate in the same direction.

8. A robotic surgical tool comprising:
a first pulley and a second pulley;
a first receptacle coupled to the first pulley;
a second receptacle coupled to the second pulley;
a first end effector removably coupled to the first receptacle by a first spring latch;
a second end effector removably coupled to the second receptacle by a second spring latch;
a shaft having a distal end to extend the first and second end effectors into a surgical site;
an interface base coupled to a proximal end of the shaft, the interface base to couple to a robotic slave to control the first and second end effectors, the interface base including a first spool to control the first end effector and a second spool to control the second end effector;
a first cable loop routed in the shaft between the first pulley and the interface base, the first cable loop coupled to the first pulley and having a first end wrapped around the first spool of the interface base in a first direction and a second end wrapped around the first spool in a second direction opposite the first direction to control the first end effector; and
a second cable loop routed in the shaft between the second pulley and the interface base, the second cable loop coupled to the second pulley and having a first end wrapped around the second spool of the interface base in a first direction and a second end wrapped around the second spool in a second direction opposite the first direction to control the second end effector;
wherein the first and second spring latches are fastened to the first and second end effectors at the first pivot axis located at a fastener, and the first and second spring latches are cantilevered at the fastener to hold the first and second end effectors coupled to the first and second receptacles;
wherein the first pulley controls the rotation of the first end effector about a first pivot axis and the second pulley controls the rotation of the second end effector about the first pivot axis together to open and close the jaws of the first and second end effectors or yaw the first and second end effectors together.

9. The robotic surgical tool of claim 8, wherein
the first receptacle is a first half receptacle,
the second receptacle is a second half receptacle, and
the first end effector and the second end effector are rotatably coupled together by a fastener.

10. The robotic surgical tool of claim 9, wherein
the robotic surgical tool is an electro-surgical tool,
the first and second end effectors are formed of a conductive material and electrically coupled together,
the interface base includes an electrical connector to couple to a generator, and
the robotic surgical tool further includes
a wire having a first end coupled to the electrical connector, the wire routed down the shaft to the first or second receptacle, the wire having a second end to electrically couple to at least one of the first or second end effectors for electro-cautery.

11. The robotic surgical tool of claim 8, wherein
the robotic surgical tool is an electro-surgical tool,
the first and second end effectors are formed of a conductive material and electrically isolated from each other,
the interface base includes an electrical connector with a first terminal and a second terminal to couple to a generator, and
the robotic surgical tool further includes
a first wire having a first end coupled to the first terminal of the electrical connector,
a second wire having a first end coupled to the second terminal of the electrical connector,
wherein the first and second wires are respectively routed down the shaft to the first and second receptacles, the first wire has a second end electrically coupled to the first end effector and the second wire has a second end electrically coupled to the second end effector for electro-cautery.

12. The robotic surgical tool of claim 8, further comprising:
a mechanical wrist coupled between the first and second receptacles and the shaft, the mechanical wrist having a first joint for a first degree of freedom and a second joint for a second degree of freedom, the first joint coupled to the shaft and the second joint coupled to the first joint and the first and second receptacles.

* * * * *